(12) United States Patent
Mershin et al.

(10) Patent No.: US 10,945,654 B2
(45) Date of Patent: Mar. 16, 2021

(54) METHODS, SYSTEMS, AND APPARATUS FOR SELF-CALIBRATING EEG NEUROFEEDBACK

(71) Applicant: Massachusetts Institute of Technology, Cambridge, MA (US)

(72) Inventors: Andreas Mershin, Cambridge, MA (US); Thrasyvoulos Karydis, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 232 days.

(21) Appl. No.: 15/043,909

(22) Filed: Feb. 15, 2016

(65) Prior Publication Data

US 2016/0235324 A1 Aug. 18, 2016

Related U.S. Application Data

(60) Provisional application No. 62/116,423, filed on Feb. 14, 2015.

(51) Int. Cl.
*A61B 5/375* (2021.01)
*A61B 5/00* (2006.01)

(52) U.S. Cl.
CPC ............ *A61B 5/375* (2021.01); *A61B 5/4824* (2013.01); *A61B 5/6803* (2013.01);
(Continued)

(58) Field of Classification Search
None
See application file for complete search history.

(56) References Cited

U.S. PATENT DOCUMENTS

2005/0018858 A1   1/2005 John
2007/0208263 A1*  9/2007 John ................... A61B 5/0452
                                                           600/509
(Continued)

FOREIGN PATENT DOCUMENTS

WO   WO 2014190414 A1 * 12/2014 .......... A61B 5/0476

OTHER PUBLICATIONS

Csikszentmihalyi, Mihaly (1990). Flow : the psychology of optimal experience (1st ed.). New York: Harper & Row. ISBN 9780060162535, p. 242.

*Primary Examiner* — Etsub D Berhanu
(74) *Attorney, Agent, or Firm* — Flachsbart & Greenspoon, LLC; Robert Greenspoon

(57) ABSTRACT

Methods, systems, and apparatus implementing a generalizable self-calibrating protocol coupled with machine learning algorithms in an exemplary setting of classifying perceptual states as corresponding to the experience of perceptually opposite mental states (including pain or no pain) are disclosed. An embodiment presented represents inexpensive, commercially available, wearable EEG sensors providing sufficient data fidelity to robustly differentiate the two perceptually opposite states. Low-computational overhead machine learning algorithms that can be run on a mobile platform can be used to find the most efficient feature handles to classify perceptual states as self-calibrated by the user. The invention is generalizable to states beyond just pain and pave the way towards creating EEG NFB applications targeting arbitrary, self-calibrated perceptual states in at-home and wearable settings.

9 Claims, 18 Drawing Sheets

(52) U.S. Cl.
CPC .......... *A61B 5/6831* (2013.01); *A61B 5/7257* (2013.01); *A61B 5/7267* (2013.01); *A61B 5/743* (2013.01)

(56) References Cited

U.S. PATENT DOCUMENTS

| | | | |
|---|---|---|---|
| 2008/0249430 A1* | 10/2008 | John | A61B 5/0476 600/544 |
| 2010/0249638 A1* | 9/2010 | Liley | A61B 5/0476 600/544 |
| 2012/0130266 A1 | 5/2012 | Mathan et al. | |
| 2013/0184603 A1* | 7/2013 | Rothman | A61B 5/7264 600/544 |
| 2014/0377727 A1* | 12/2014 | Yom-Tov | A61B 5/165 434/236 |

* cited by examiner

METHODS, SYSTEMS, AND APPARATUS FOR SELF-CALIBRATING EEG NEUROFEEDBACK

This application claims the benefit of U.S. Provisional Patent Application No. 62/116,423, filed Feb. 14, 2015. This application hereby incorporates by reference U.S. Provisional Patent Application No. 62/116,423 in its entirety.

TECHNICAL FIELD OF THE INVENTION

The present invention relates to sensors and methods for brain computer interfaces (BCI), biofeedback (BFB) and neurofeedback (NFB) as both diagnostic and therapeutic tools based primarily on Electro-encephalography (EEG) but extending to other modalities as well (such as magnetoencephalography—MEG, thermography and similar).

BACKGROUND OF THE INVENTION

Electro-encephalography consists of measuring small voltage deviations from a baseline between a common ground electrode and sensors in contact with the scalp, or behind the ears. The sensors produce time series traces of voltage amplitude called electroencephalographs (EEG). There are several established methods for employing EEG for therapeutic biofeedback and neurofeedback in clinical settings and these have been evolving in their capacity and scope since the late 1970s. United States Food and Drug Administration (FDA)-approved applications of EEG neurofeedback techniques range from attention and focus improvements in Attention Deficit (Hyperactivity) Disorder (ADHD/ADD) patients to in-office treatments of depression and anxiety. The last half-decade has seen an intensifying movement towards bringing these modalities out of the clinician's office to the patient's home. Also, the trend to use EEG neurofeedback for non-therapeutic performance enhancement such as alertness, productivity, focus and calmness have been increasing, facilitated by the proliferation of new, inexpensive, few-electrode EEG systems such as the Neurosky Mindwave™, the Mellon™, and the Muse™ headbands that also perform robust onboard digital signal processing to filter out noise and compute Fast Fourier Transforms (FFT) in real time. These and other headbands, coupled to PC, tablet or smartphone applications that handle the brain-computer interfaces including data acquisition, signal processing and feedback visualization have been proliferating with hundreds of apps available for download for an ever increasing number of headband sensors meant to be used as "brain training" aids. Despite rapid increases in sensor fidelity and data acquisition and processing rates efficacy of the method has barely changed since the 70s.

This is in part because the variability inherent in human brain waves and skull shapes and sizes and brain morphology is high from human to human. With few exceptions (such as calmness and alertness), self-reported perceptual states robustly corresponding to extractable features in a person's own EEG data are not easily transferable to another person or even to the same person on a different day without elaborate precision in placing multiple scalp electrodes.

U.S. Patent Publication No. 2012/0130266 to Mathan et al. ("Mathan") describes a system and method for estimating cognitive efficacy of an individual. EEG data from EEG sensors coupled to the individual are collected while the individual is performing the variety of tasks. The EEG data are supplied to a trained classifier that generates an estimate of cognitive effort of the individual for each of the plurality of tasks performed by the individual. Mathan Abstract. The application area Mathan is concerned with is estimating cognitive function to assess the progress of individuals with mild traumatic brain injury (MTBI) over the course of rehabilitation and/or post-injury cognitive impairment. Mathan, at [0002]-[0005]. While Mathan discloses using a trained classifier to automatically classify individual cognitive states in real-time (Mathan, at [0021]-[0023]), the classification performed is merely of cognitive effort and not different arbitrarily defined categories, such as "pain/no-pain" "up/down" or "zone/no-zone". In Mathan, the baseline cognitive effort data that are collected while the individual performs various tasks are used as the basis for constructing the classifier. Mathan, at [0024]. Mathan's classifier is not self-calibrating, because one is not free to define arbitrary states as "up" and "down" that correspond to the individual.

Note that, the "up" and "down" are generic names for "opposite" states that can be anything, including not normally associated with being opposites of each other in any common sense kind of way. For instance "up" may designate "right time to be involved in day trading" while "down" may designate "right time to be at the gym". These are not necessarily the plain and ordinary meaning of "opposites" of each other, but since these are completely user-defined the invention is agnostic as to what the user assigns as opposites. The machine learning and SCP works just as well upon training.

The application area of the present invention solves the long-felt need of being able to accurately determine a specified category of experiencing/perceiving at a certain time. For example, if a nurse or doctor is deciding whether to administer pain medication to a patient, the nurse or doctor will only do so if the classifier determines that the patient is in fact experiencing pain above an acceptable threshold, previously determined by the patient themselves during calibration. In this particular application area, the benefit of the invention is the prevention of addiction, by elimination of unnecessary administrations of higher dose pain medication, and decreasing the likelihood of accidental overdoses at the hospital as well as a result of at home use of legal or illicit drugs before or after pain medications prescriptions run out. Additionally, the patient may learn how to control their own pain perception at least to a point using any number of known neurofeedback techniques that are expected to be much more efficacious after SCP have been applied compared to traditional methodologies.

SUMMARY OF THE INVENTION

A novel self-calibrating protocol (SCP) method to classify preception states that can, for example, correspond to the experience of "pain" or "no pain" is described. The invention concerns SCP and the use of existent machinery, both hardware and software, to make a new modality and slew of applications possible. Pain is one example. However, the invention is widely applicable as a generic, generalizable method. Machine learning algorithms are a type of technology that SCP can be coupled with to implement the invention.

A largely overlooked fact in the relevant EEG scientific literature is that commercially available, wearable EEG sensors provide sufficient data fidelity to robustly differentiate two "opposite" perceptual states. As noted previously, "opposite" states can be anything, including not normally associated with being opposites of each other in any "common sense" assignment. Herein described are first steps towards a versatile and reliable platform for individualized EEG neurofeedback, using SCP to bypass the pitfalls of using "normed" neurophysiological states, and paving the way towards personalized therapies and brain training that is self-calibrated to arbitrary perceptual states corresponding to a wide variety of individual needs.

In illustrative embodiments of this invention, a versatile platform detects a wide range of brain states and automates the production of neurofeedback interfaces. This platform technology works upon user calibration leveraging supervised, semi-supervised and unsupervised machine learning algorithms to facilitate low-computational overhead applications for clinical and at-home use. In illustrative implementations of this invention, self-calibrating protocols (SCP) are applied to EEG and EEG-based NFB. In illustrative implementations, arbitrary perceptual states are assigned to recorded EEG traces from an individual that are later used as basis for a neurofeedback training to the same individual without the need for visits to the clinician's office or outsourcing personalization of EEG data to commercial quantitative EEG processing services. In illustrative implementations, this invention allows for the at-home use of modern EEG sensing headbands coupled to consumer grade electronics such as PCs, tablets and smartphones.

The classifier can also be a multi-class classifier which classifies non-binary brain states. Calculating the classifier can consist of determining the posterior probability for both the desired (up) and undesired (down) perceptual states as well as intermediate states in between the two extremes.

DETAILED DESCRIPTION OF INVENTION

SCP Principle

Figure 1:
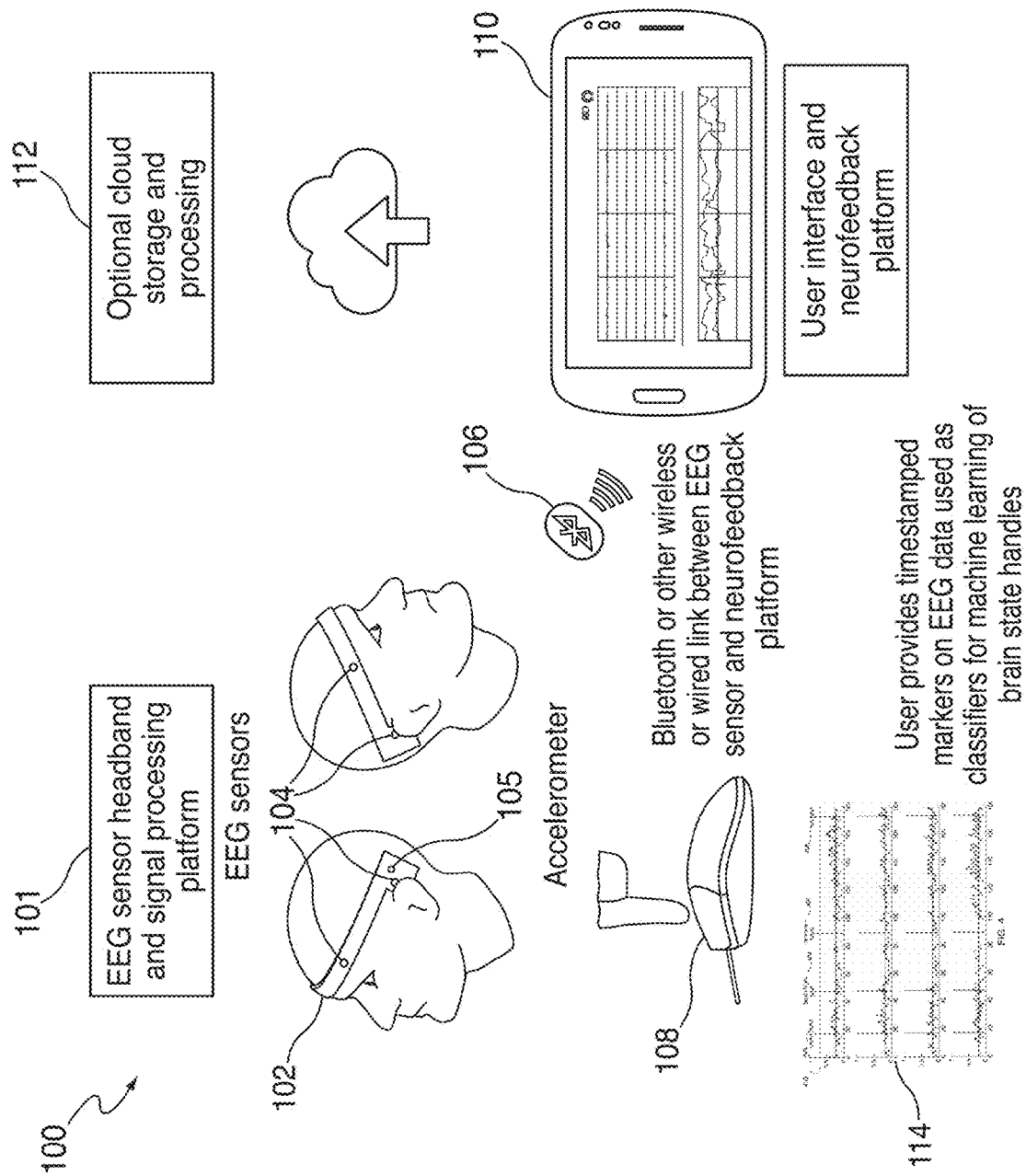
FIG. 1 is an overview of an exemplary system setup with optional cloud storage and signal processing link showing placement of EEG sensor headband.

The principle behind self-calibrating protocols (SCP) is that of time-stamping regions in a time-series waveform input designating areas of "up" and in one mode by default calling everything else "not up" or in an enhanced mode using another designation for regions timestamped as "down". Once regions in the time series of the minimally processed EEG signal have been identified in this manner, off-the shelf machine learning algorithms are deployed to identify minimal handles to use in either traditional neurofeedback settings (replacing the "up" and "down" ordinarily calibrated to an average by the now personally selected features). The key advantage of SCP is that the NFB no longer needs to correspond to a mechanistically defined neurological correlate. In other words, it is no long necessary to identify a specific ratio of brain wave frequencies as corresponding to a universally applicable "calm" or "alert" or other perceptual state. One is free to define arbitrary states as "up" and "down" and it is no longer necessary for one to be the functional opposite of the other. Instead of calibrating a person's brain to a population average, SCP allows to calibrate to that person's individual brain morphologies and perceptional indiosyncracies.

The pseudocode of the SCP process is as follows:

Step 1: Learn YOUR brain wave patterns
  User indicates actively or passively when the perceptual state is in "desired='up'" or "undesired='down'" status
  Active: user presses a button; Passive: app records proxy (as examples, words typed per minute, $ made per rapid trade)

Step 2: SCP allows to alert, predict, train
  Alert when your perceptual state is in your desired/ undesired state
  Predict when you're going to be in that state (advance notice could be shorter or longer depending on "state" definition)

Train your brain to get back into desired perceptual state ideally "on command" using neurofeedback-loop game The protocol can be continuously monitored and adapted, to accommodate, for example, the fact that a person's brain changes over time (a recurring business model implication). The benefits of the protocol are increased efficacy, agnosticism to desired state: the app doesn't "care" if you want to track and improve focus, calmness, productivity, or physical performance, and the user defines the desired/undesired state.

The self-calibrating protocol can also implement a multi-class classifier which classifies non-binary perceptual states. Calculating the classifiers parameters consist of determining the maximum posterior probability for both the desired (up) and undesired (down) states, upon training.

Self-Calibrating Protocols (Software)

The use of EEG to treat various disorders through neurofeedback—giving the client real time information about their EEG and using operant conditioning is standard practice. It works by reinforcing changes in the EEG back to a norm. A norm is typically established with quantitative EEG, or Brain Electrical Activity Mapping (BEAM)—which attempts to identify regions of the brain that may be functioning abnormally in various disorders by processing the raw EEG data, mapping and comparing it with a "normative" database of controls. Traditionally, these areas are then targeted for treatment by neurofeedback. Case reports and clinical trials going back to the 1970s argue the potential efficacy of neurofeedback, however, problems including lack of standardized protocols and difficulty with designing sham trials (even sham treatment may evoke reward pathways important in learning and memory, thereby confounding results) has left the methodology with confusing results and a poor reputation. In illustrative implementations, the invention described herein: (a) defeats the problems associated with cross-applicability of calibration achieved against a wide average in favor of self-calibrating protocols; and (b) decouples any particular brain region or putative physiological mechanism from the application of neurofeedback as a brain training tool, allowing the user/client to assign arbitrary experiences to perceptual states designated as "up" and "down" and train for one against the other.

In illustrative implementations, the present invention provides a versatile and reliable platform for EEG neurofeedback unlimited by well-characterized neurophysiological states obtained from calibration to other users. In various embodiments, the invention employs a headband EEG sensor connected to a signal processing and visualization system in the form of a PC, tablet or smartphone platform that runs the digital signal processing, machine learning and user feedback interface. Optionally (historical) data storage and analysis takes place off-platform (in the cloud) via the Internet. In some cases, scalp electrodes are made by embedding conducting electrodes and flex circuitry into Polydimethyl Siloxane (PDMS) elastomers.

EEG Sensors Coupled to Other Sensing Modalities

In certain embodiments, the present invention arranges a series of sensors in such a way that the overall system generates a dynamic pattern detection signature, reducing the prior tuning and calibration to other user's requirements, increasing the ability to personalize EEG neurofeedback applications and lowering the computational power requirements of the analysis hardware.

In some embodiments, the method or system employs one or more sensors that provide baseline measurements. In some embodiments, these include sensors measuring acceleration and gyroscopes to aid in the rejection of spurious signals due to maceration, movement, head tilting, etc. In some implementations, other sensor modalities such as heart rate, blood oxygenation, breath depth and duration, blood pressure, blood sugar and other physiological parameters including other methods of brain monitoring such as MagnetoEncephalography and Thermography are coupled to the primary EEG signal to aid in determining specific perceptual states. The system further comprises data analysis hardware and software to identify through iterative measurements electrical inputs that provide indicative output signals.

Two Modes of Operation

In illustrative implementations, the invention is operated in at least two distinct modes: Neurofeedback Brain Training Mode and Neurofeedback Brain State Predictive Mode.

1. Neurofeedback Brain Training Mode

The invention in various aspects provides algorithms and methods for machine learning of EEG signal handles that robustly correspond to reproducible user perceptual states and experiences using improved processes for such detection and refinement via a number of previously established methods such as neural networks, supervised machine learning, pattern recognition and dynamic background reduction or pattern matching (distinct from pattern recognition) and others.

The methodology for self-calibration is versatile, in that the EEG sensors can be configured for the detection of a wide range of perceptual states, not limited to "opposites" such as calmness vs. anxiety. Thus, in various embodiments, the present invention provides methods and systems for detection, prediction and neurofeedback brain training to arbitrary user-defined self-calibrated perceptual states identified by flexible EEG signal handles, not limited to averages obtained on populations of other users.

In certain embodiments, the recognition is accomplished through signal pattern matching, defeating the problems associated with pattern recognition in noisy, unknown backgrounds.

When operated in brain training mode, the technology is capable of presenting a classical EEG neurofeedback interactive "game" tuned to drive the brain towards a user-defined, self-calibrated EEG state that can have an arbitrary physiological substrate. For instance "flow" or "creativity" or "curiosity" or "rote memorization" states as defined and experienced by the user can be defined as the "up" state while others such as for instance "boredom", "writer's block" or even emotional states such as "sadness" and "anger" can be used as the corresponding "down" states without these being neurophysiologically or functionally related or even loosely defined as the opposites to each other.

2. Neurofeedback Brain State Predicting Mode

When operated in prediction mode, upon completion of the training and refinement phases, the technology is capable of continuously and dynamically monitoring the EEG based handles predicting of an impending perceptual state of interest whether it is "up" or "down". Depending on the quality of the prior machine learning and refinement phases, and the nature of the target perceptual states, the time between prediction and entering the state varies from seconds to minutes.

Illustrated by Example

1. Example Use Case 1: (NFB Brain Training Mode)

Step 1

Recording arbitrary desired perceptual state for personal use. User wears the headband and activates the user interface software on, say, the iPad that is connected via Bluetooth to a commercial (e.g. see FIG. 1 for system overview and FIG.

6 for exemplary user interface (UI) display of Muse™ headband) or custom made headband.

Figure 17:
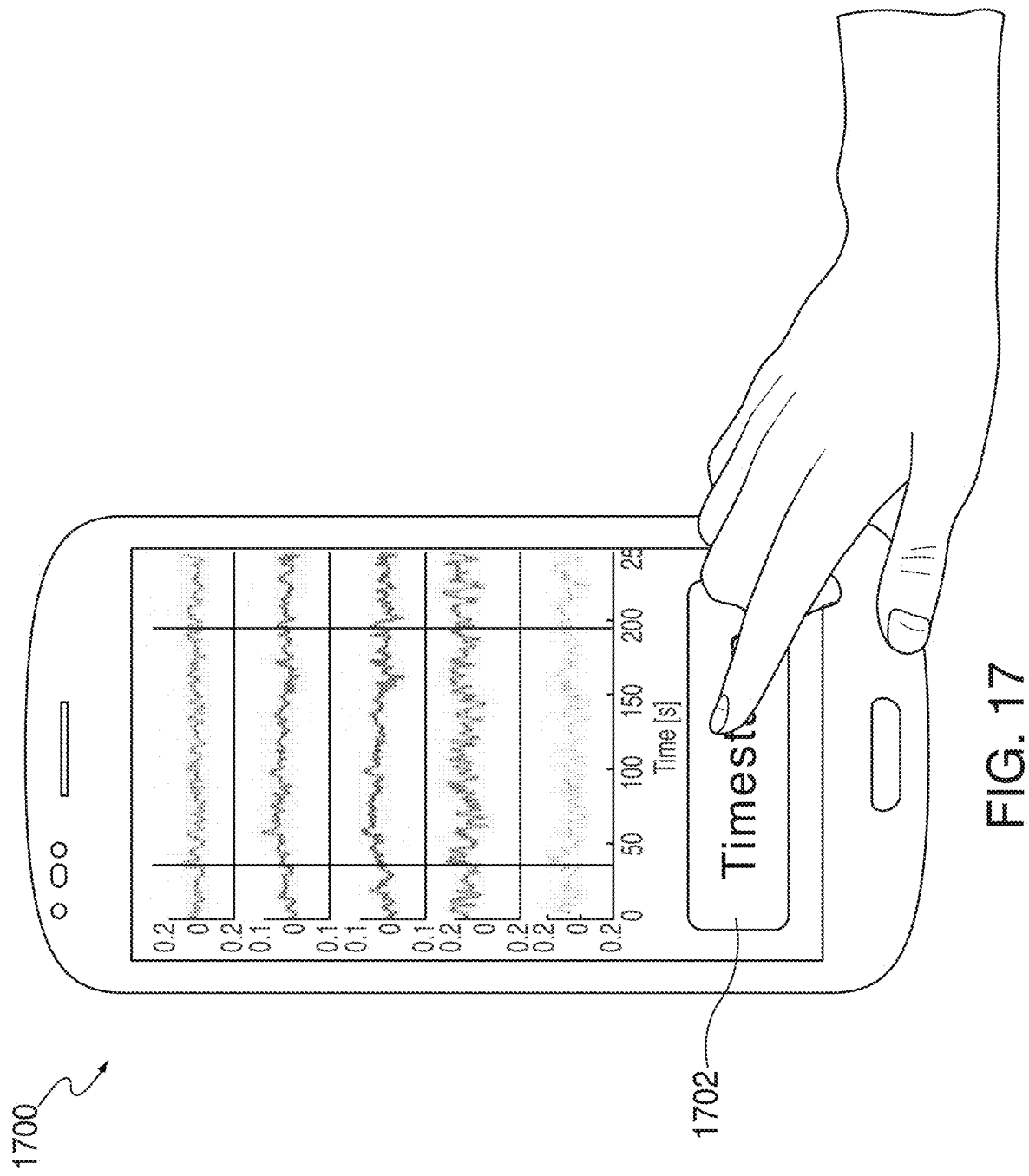
FIG. 17 shows an example mobile device used for timestamping by a user.

FIG. 1 shows the components of the SCP method, system and apparatus (100). It comprises an EEG sensor headband and signal processing platform 101. A headband 102, worn by the user, comprises EEG sensors 104 and an accelerometer 105. There is a Bluetooth or other wireless or wired link (collectively, 106) between the EEG sensors 104 and user interface and neurofeedback platform 110. The user interface and neurofeedback platform 110 can, for example, be a mobile device (FIG. 17 shows a mobile device 1700 that includes an easily findable timestamp button 1702). The user provides timestamped markers on EEG data used as classifiers for machine learning of perceptua state handles (item 114). This can be done via a mouse 108 or via an input on the user interface and neurofeedback platform 110. The SCP invention also comprises optional cloud and storage and processing, item 112.

Figure 6:
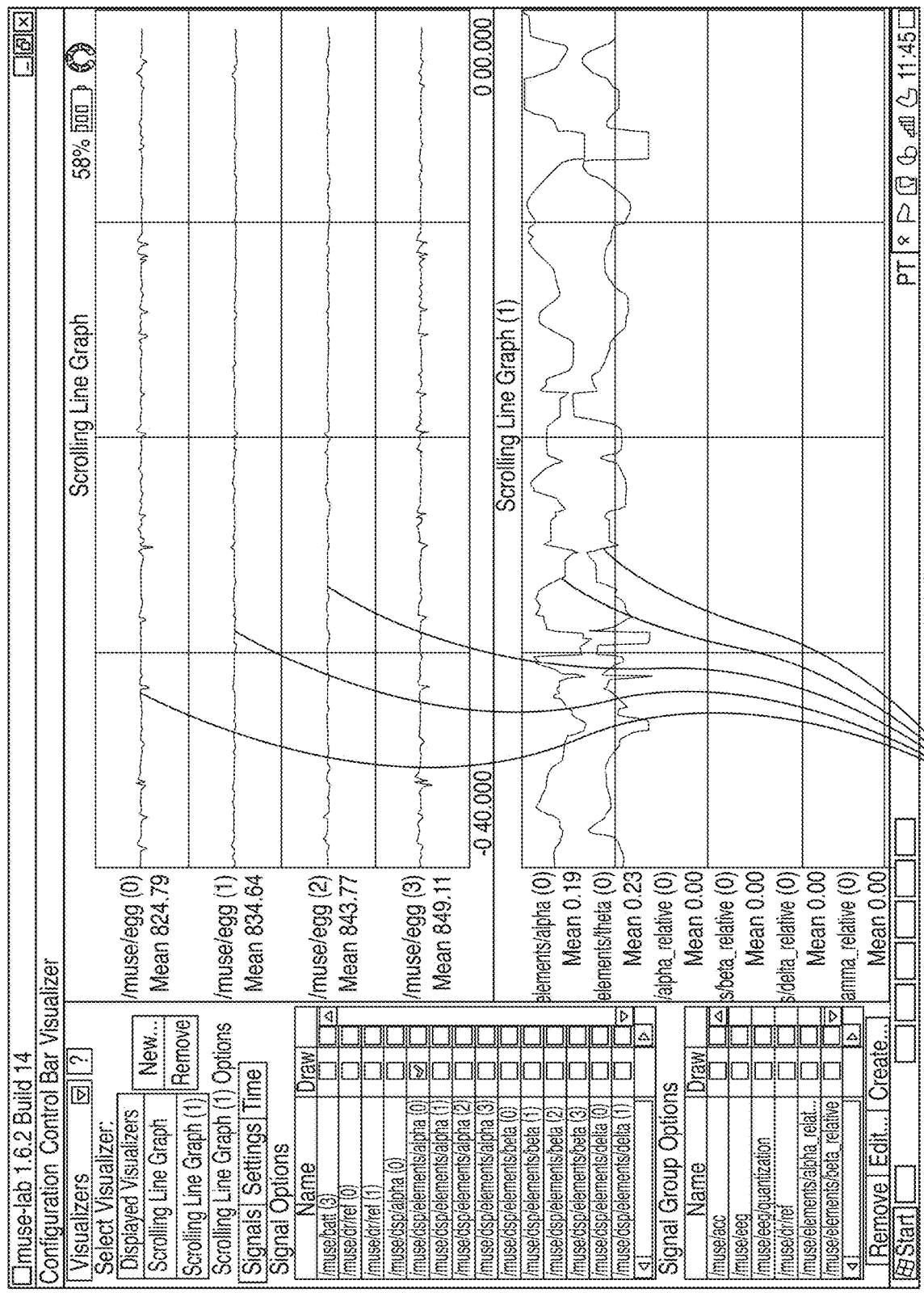
FIG. 6 is a screenshot of Muse™ EEG headband developer user interface.

FIG. 6 is an exemplary user interface (UI) display of Muse™ headband, containing one or more scrolling line graphs 602.

Step 2

Upon ensuring good signal acquisition from all EEG sensors and optionally additional sensors (such as accelerometers, gyroscopes heart rate monitors etc.) the user engages in a complex mental activity with sensitivity to tight balances between focus and concentration and diffuse global awareness. In some cases, the activity has a nearly real-time report allowing the scoring of the efficacy of decision making, for instance rapid stock trading as routinely done by hedge fund managers.

Step 3

As the trader enters the self-reported "zone" which can be also backed up by trading data showing profitable trades being made consistently above background, the user either manually sets a time stamp marking the onset of "the zone" state or the custom software that has pre-set limits of performance automatically triggers once these limits are reached to mark (timestamp) the EEG trace as entering the desirable "zone" perceptual state as a generalized "up". Upon exiting the state via the reverse steps, the timestamp is added as a generalized "down". Several iterations of timestamping "up" and "down" states complete the self-calibration phase (item 212 of FIG. 2).

Figure 2:
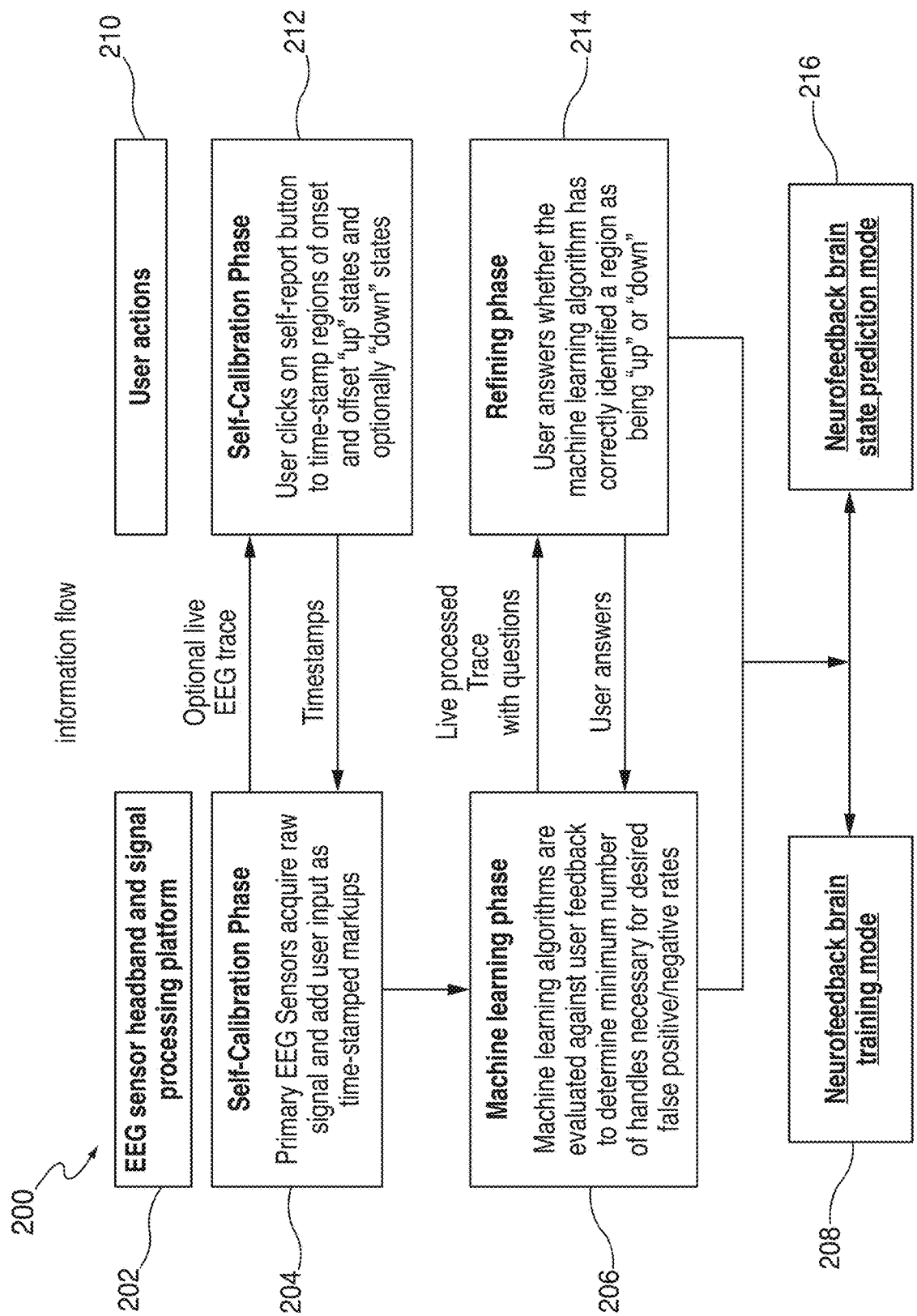
FIG. 2 is an example system overview outline, showing communications flow and two modes of operation.

FIG. 2 shows the information flow 200 of the system, including the various hardware components. The information flow includes an EEG sensor headband and signal processing platform 202. In self-calibration phase 204, primary EEG sensors acquire raw signals and add user input as time-stamped markers. In machine learning phase 206, machine learning algorithms are evaluated against user feedback to determine the minimum number of handles necessary for desired false positive/negative rates. User actions 210 are part of the self-calibration phase 212, in which the user clicks on a self-report button to time-stamp regions of onset and offset "up" states and optionally "down" states. In the refining phase 214, the user answers whether the machine learning algorithm has correctly identified a region as being "up" or "down." The information flow also comprises a neurofeedback training mode 208 to train the machine learning algorithm and neurofeedback perceptual state prediction mode 216 where the machine learning algorithm is applied. Self-calibration phase 204 sends optional live EEG traces to self-calibration phase 212, and self-calibration phase 212 sends timestamps to self-calibration phase 204. Self-calibration phase 204 feeds information to the machine learning phase 206. The machine learning phase 206 sends live processed trace with questions to the refining phase 214, and refining phase 214 sends user answers to machine learning phase 206. Both the machine learning phase 206 and refining phase 214 provide information to neurofeedback brain training mode 208 and neurofeedback brain state prediction mode 216, and the neurofeedback brain training mode 208 and neurofeedback brain state prediction mode 216 are in communication with each other.

Step 4

Next follows the machine learning phase (which in some cases starts concurrently with the first user provided timestamp). During this phase is the self-calibrating protocol is such that a number of machine learning algorithms are tried alternatively treating the data stream as the training and testing set dynamically.

Step 5 (Optional)

Figure 8:
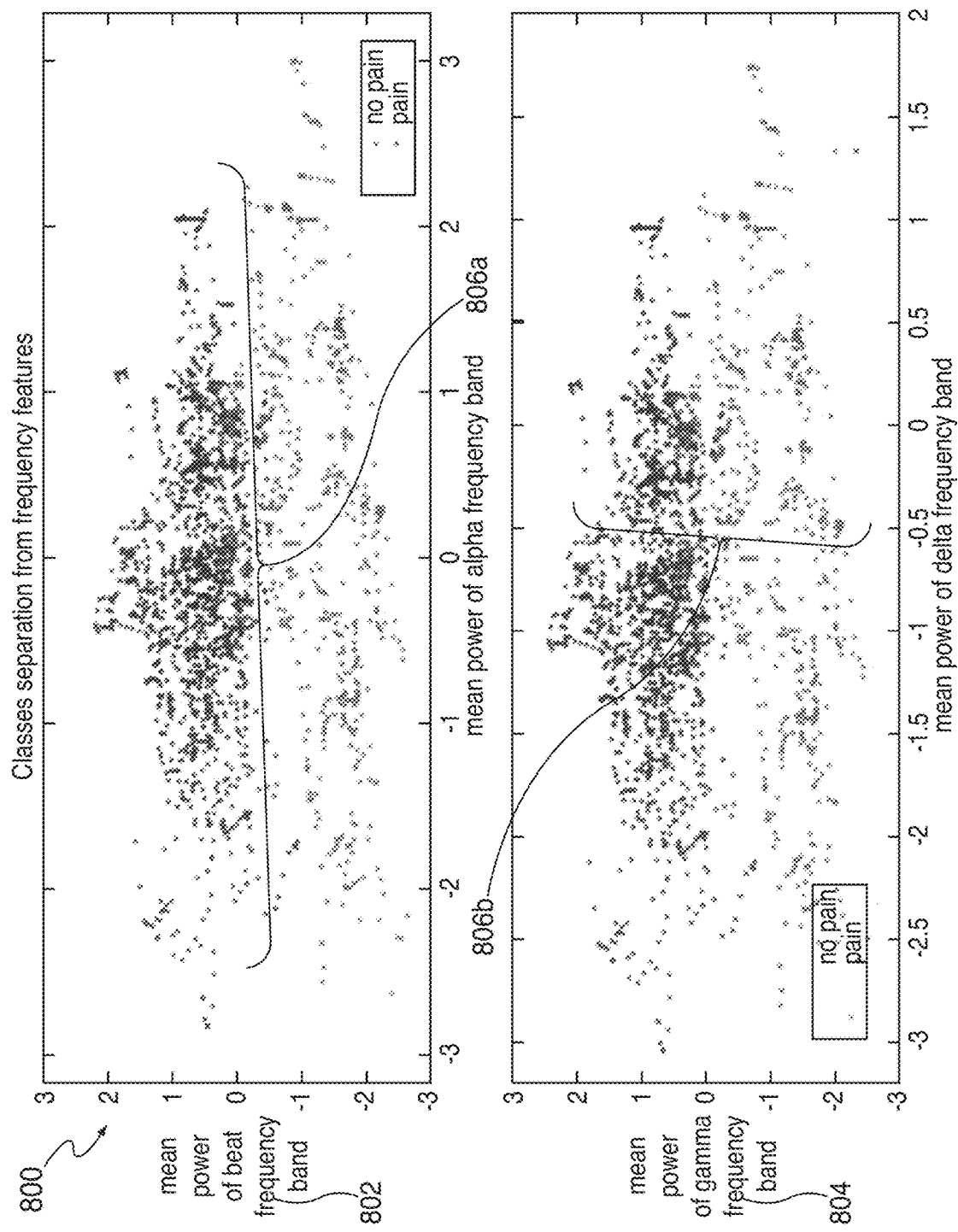
FIG. 8 is scatter plots of pairs of mean power in different bands (alpha=9-13 Hz, beta=13-30 Hz, gamma 30-50 Hz, delta 1-4 Hz, theta=5-9 Hz) grouped by class (in this example the two classes are user-reported class "pain" and "no pain"), showing sufficient separation for use with linear classifiers.
Figure 9:
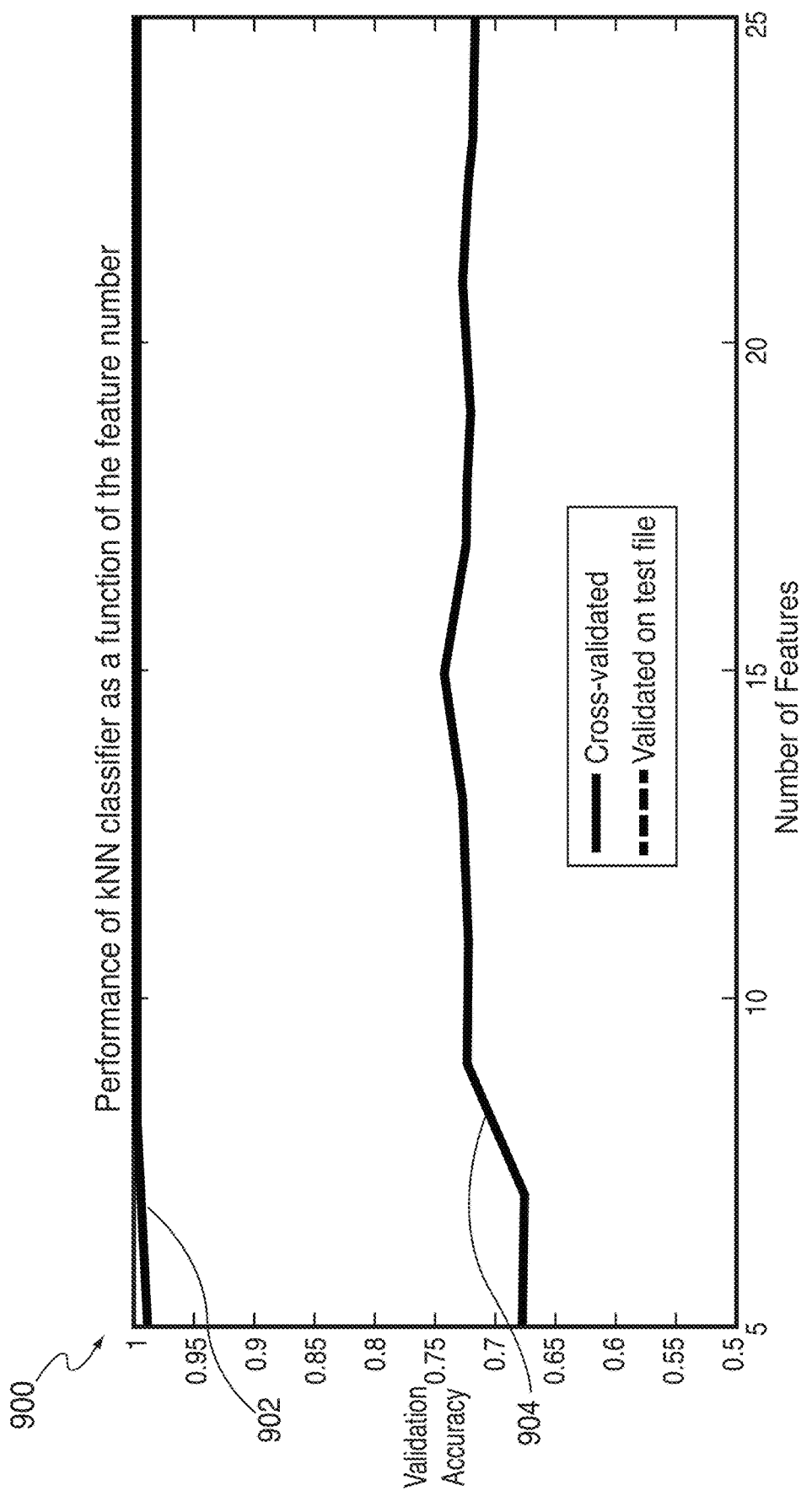
FIG. 9 is performance of k Nearest Neighbors classifier (kNN) as a function of the number of features, cross validated: training set from same user folded five times, validated on the test file: classifier trained on user A, tested on data from user B.
Figure 10:
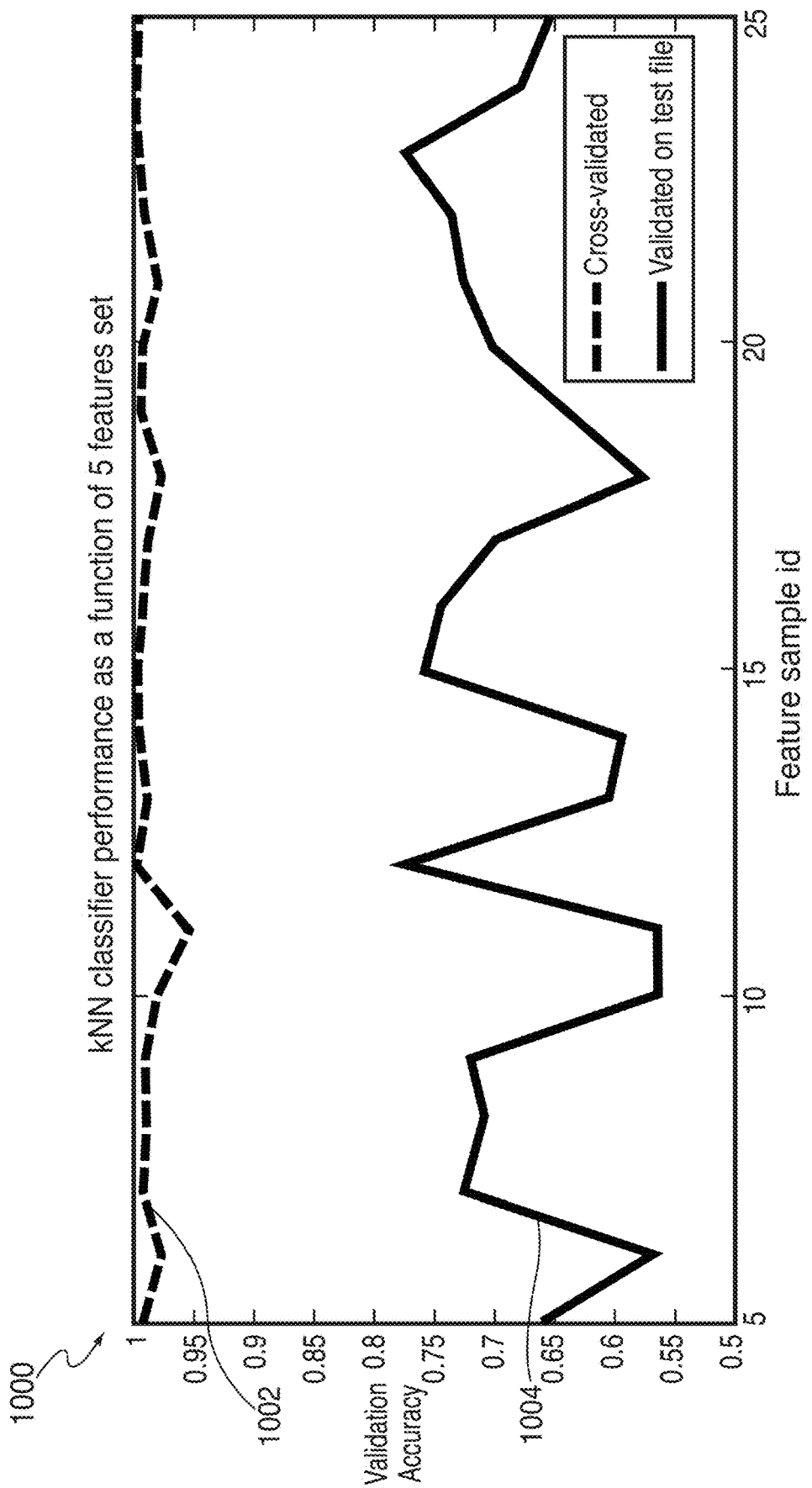
FIG. 10 is performance of k Nearest Neighbors classifier (kNN) for various combinations of five-feature sets.

To aid in refining the handle-finding by the machine learning algorithms the protocol calls for starting to guess states and asking the user to confirm correct or incorrect or N/A status of guess. This "refinement" phase is optional and will increase fidelity the more it is practiced. In testing the prototype deployment with the "up" perceptual state assigned to "no pain" and "down" assigned to "high pain" (induced by submerging one of user's palm into ice water for a few seconds FIG. 3,4,5,7) seconds of computation on a MacBook Pro running MATLAB (using exemplary code attached as separate files to patent) resulted in over 85% fidelity in recognizing pain versus no pain states in a stationary setting (FIGS. 8,9,10). While the function of this system with "up" and "down" perceptual states was defined as the well-controlled "pain"/"no pain" the same methodology is extendible to "good trades"/"bad trades" upon coupling to a near-realtime reporting/scoring system such as those found in high frequency stock trading.

Figure 3:
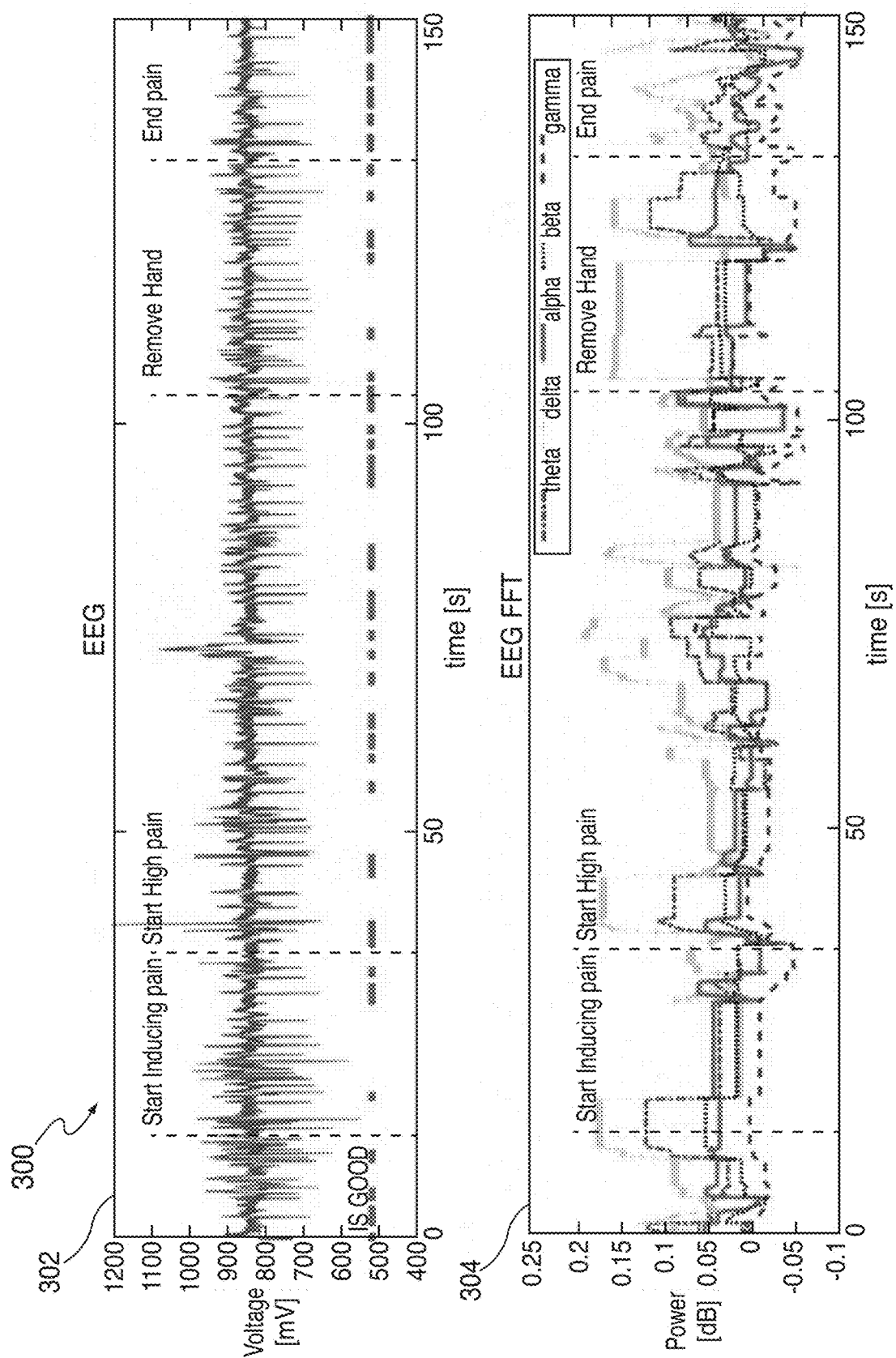
FIG. 3 is an example of marked up raw (upper trace) and frequency processed (lower traces) EEG output.
Figure 4:
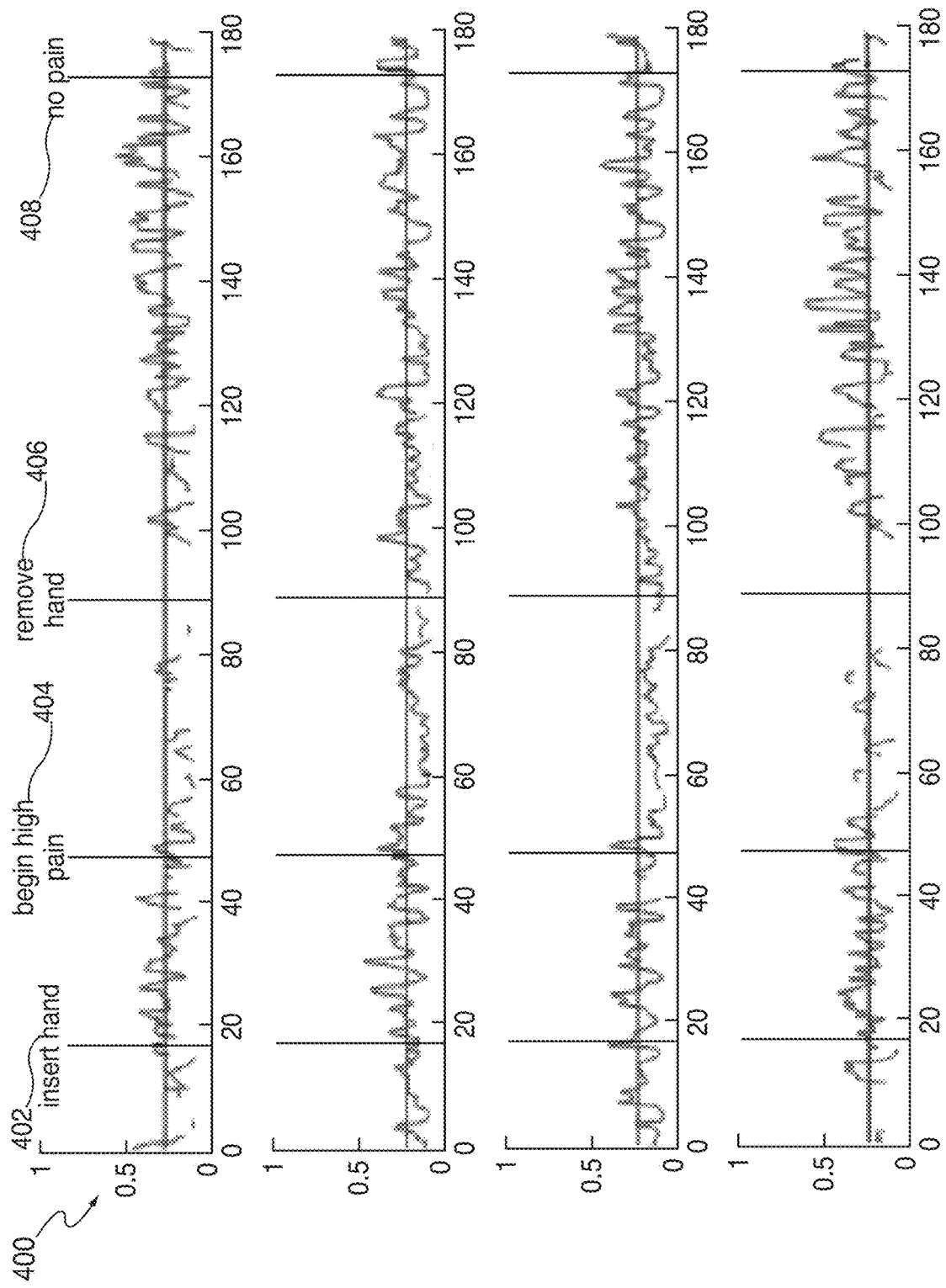
FIG. 4 is exemplary raw EEG signals (all four muse headband sensors) vs. time (sec) salient events timestamped by a user.
Figure 5:
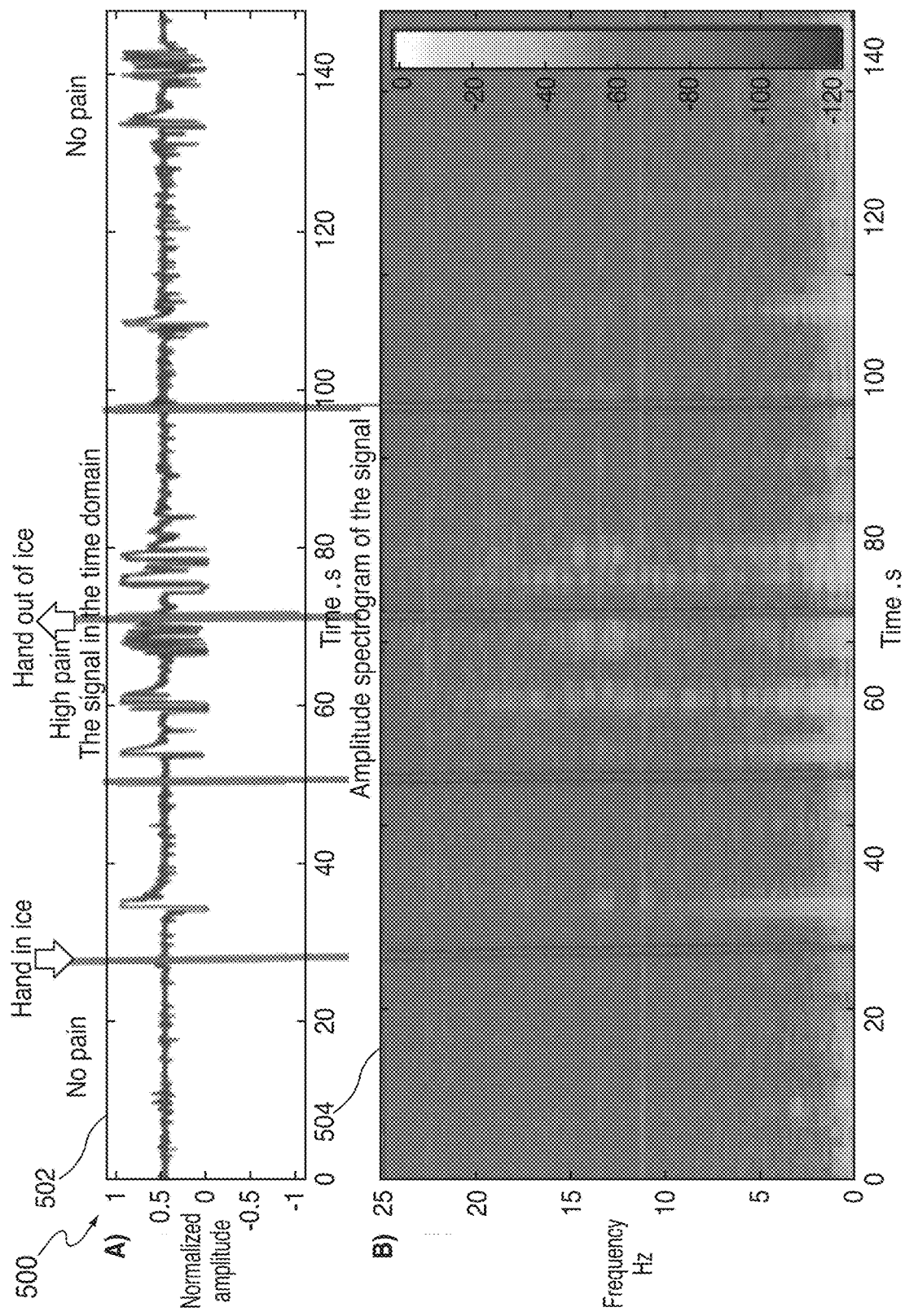
FIG. 5 is A) Exemplary raw EEG signal (amplitude vs. time of rear left electrode) and B) Amplitude spectrogram of the raw EEG signal, (Short-FFT with 10 ms window).
Figure 7:
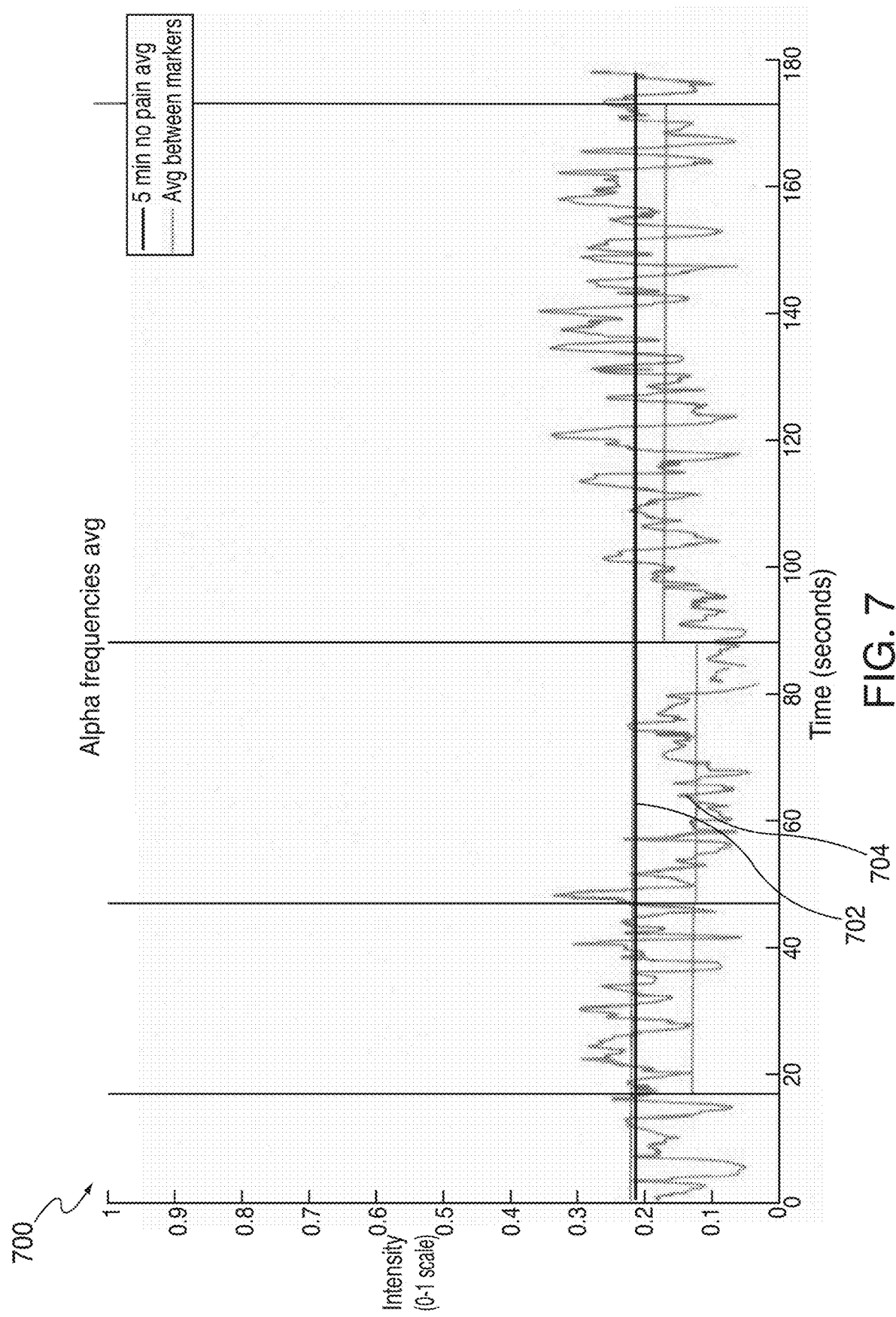
FIG. 7 is average of alpha bandpower across electrodes during high pain window (t=~45 sec-90 sec) detectably lower than other regions even in the absence of additional processing.

FIG. 3 is an example of marked up raw (upper trace 302) and frequency processed (lower trace 304) EEG output. FIG. 4 is exemplary raw EEG signals (all four muse headband sensors) vs. time (sec) salient events timestamped by a user. Four thresholds are shown, namely insert hand 402, begin high pain 404, remove hand 406, and no pain 408. In an example setup, pain cannot start before subjects insert their hand in the ice bath (so all data before insertion has a pain value of 0), and it is clear that pain is high in the moments immediately prior to when subjects remove their hands from the ice bath. FIG. 5 shows both the exemplary raw EEG signal (amplitude vs. time of rear left electrode)—item 502, as well as an amplitude spectrogram by FFT of raw EEG 256 window size—item 504. FIG. 7 shows the mean energy of alpha frequencies during high pain window (t=~45 sec-90 sec) detectably lower than other regions even in the absence of additional processing. Shown are both the 5 minutes no pain average (item 702) as well as the average between markers (item 704). FIG. 8 shows scatter plots of mean power per frequency in different bands (alpha=9-13 Hz, beta=13-30 Hz, gamma 30-50 Hz, delta 1-4 Hz, theta=5-9 Hz) grouped by class (in this example the two classes are user-reported class "pain" and "no pain"), showing sufficient separation for use with linear classifiers. Shown are both the mean power of alpha frequency band (802) as well as mean power of delta frequency band (804). The separation of "no pain" and "pain" are shown generally by hyperplanes 806a and 806b. FIG. 9 is the performance of k Nearest Neighbors classifier (kNN) as a function of the number of features, cross validated (902): training set from same user folded five times, validated on the test file (904): classifier trained on user A, tested on data from user B. FIG. 10 is the performance of kNN for various combinations of five-feature sets. Shown are cross-validated results (1002) and results validated on the test file (1004).

Step 6

To create a EEG NFB brain training user interface (UI) that uses as "up" and "down" the arbitrary trained states as described above is now straightforward: using the standard EEG NFB protocol, instead of training towards an externally derived calibrated average brain state, now the user is trained to achieve the EEG pattern that results in the one most closely resembling the handles found to be predictive during the training and optional refinement stages. This completes the exemplary embodiment this technology as used in the NFB brain training mode.

2. Example Use Case 2: (NFB Brain State Predicting Mode)

The first steps in using the invention described here in the NFB brain state predicting mode are identical up to Step 5. Instead of Step 6 as above, now the algorithm is dynamically analyzing the real time EEG stream with the aim of alerting the user either as early as possible warning that either an "up" or "down" state is about to be entered. This has clear advantages in the scenario of a rapid stock trader who can be alerted of an impending perceptual state that has previously been well correlated with bad trades so trader can take a break and avoid mistakes caused by being in a predictably inferior perceptual state as applied to high speed stock trading. Equally, being alerted to being near the beginning of a "zone" phase is valuable as now trader can enjoy a higher confidence in their decision making and maximize profits.

Setup

EEG Hardware and Signal Acquisition Software

To monitor the EEG signals from the subjects during a real-world trial, the Muse™ headband was used, which comprises of 3 reference and 4 input electrodes. The reference electrodes are located on the forehead and the input electrodes are two front (left and right of the reference) and two back above each ear. Lastly, the headband has a single accelerometer module capable of tracking 3-axis movement of the head (see FIG. 1) input from which is used to reject noisy data acquired during sudden head movements. The device performs synchronous sampling of the four electrodes with a sampling rate of 12 kHz. The data are oversampled to increase precision bits and then downsampled to 220 Hz, which is the effective output frequency for the raw EEG signal with dynamic range of 0-1.682 mVolts. An onboard digital signal processing (DSP) module performs noise filtering and a Fast Fourier Transform (FFT) on the raw EEG signal using a 256 sample window, with a step of 22 samples i.e. 10 times per second (windows overlap 90%). There are six standard frequency bands known to be good handles for EEG feature extraction and whose ratios have been shown useful in NFB training $\alpha$:9-13 Hz, $\beta$:13-30 Hz, $\gamma$: 30-50 Hz, $\delta$:5-8 Hz and $\theta$:1-4 Hz. The average power in these bands is real-time computed in hardware and sent alongside an indicator of data quality from each sensor. The raw FFT values along with the bandpower in each frequency are transmitted at 10 Hz via Bluetooth to laptop running MacOS10.10.2 and the company-supplied SDK and passed to custom signal processing algorithms written in MATLAB. The EEG signal (both raw and frequency data) processing and classification was conducted using the Statistics and Machine Learning toolkit of the MATLAB 2014b_edition. The manufacturer provided on-device computed FFTs were used filtered by the sensor data quality indicator.

Pain/No-Pain EEG Data Collection

To illustrate the benefits of the invention (as well as to test its efficacy), in one setup, data was collected from seven test subjects under identical conditions. The Muse™ headband was worn according to manufacturer's instructions and subjects were asked to sit quietly with eyes open and arm resting naturally to establish a 20 second baseline marked as "no pain". Subjects then submerged one hand into an ice water bath (kept at 0° C.) and were asked to verbally report their pain level on a scale ranging from 0 (no pain) to 10 (unbearable). Arbitrarily, a pain level of 8 was chosen as the threshold for "acute pain" which was self-calibrated to the moment subjects chose to remove their hand from the ice-bath (typically around 60 sec post-insertion and long before numbness or permanent tissue damage could result.) Subjects reported a return to level 0 within a few tens of seconds upon removal of hand from ice water. Six of seven subjects showed a uniform pain response while one exhibited unusual pain tolerance anecdotally attributed to multiple sports trauma to the hand followed by arm surgery. The EEG data were timestamped at four key positions: 1) insertion of the hand into the cold bath, 2) start of high pain 3) removal of the hand 4) end of pain. See FIGS. 11 and 12.

Figure 11:
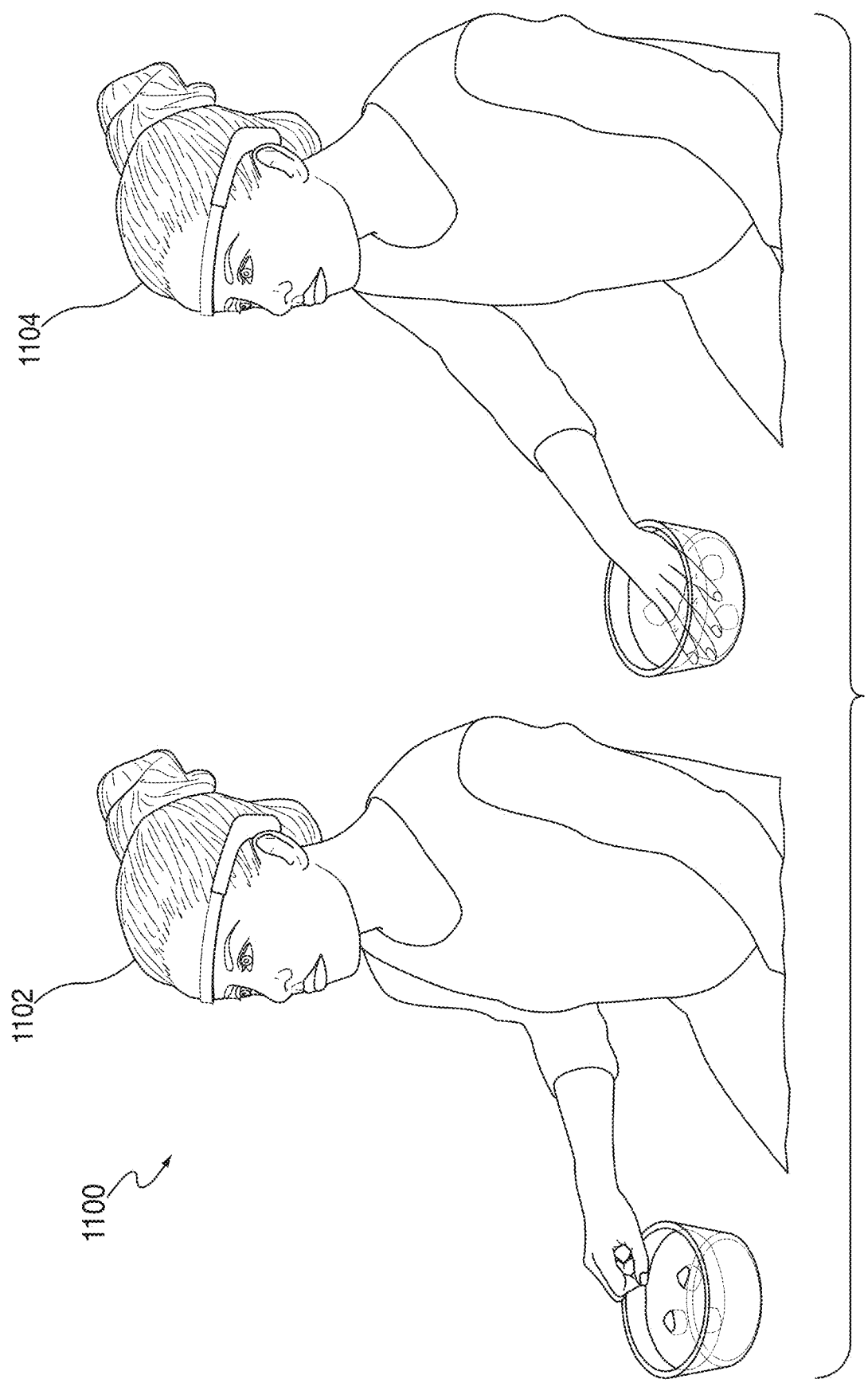
FIG. 11 is an illustration of an exemplary training phase of SCP: User is reporting when entering an undesired state and his/her EEG data is marked by the algorithm to be used for calibration.
Figure 12:
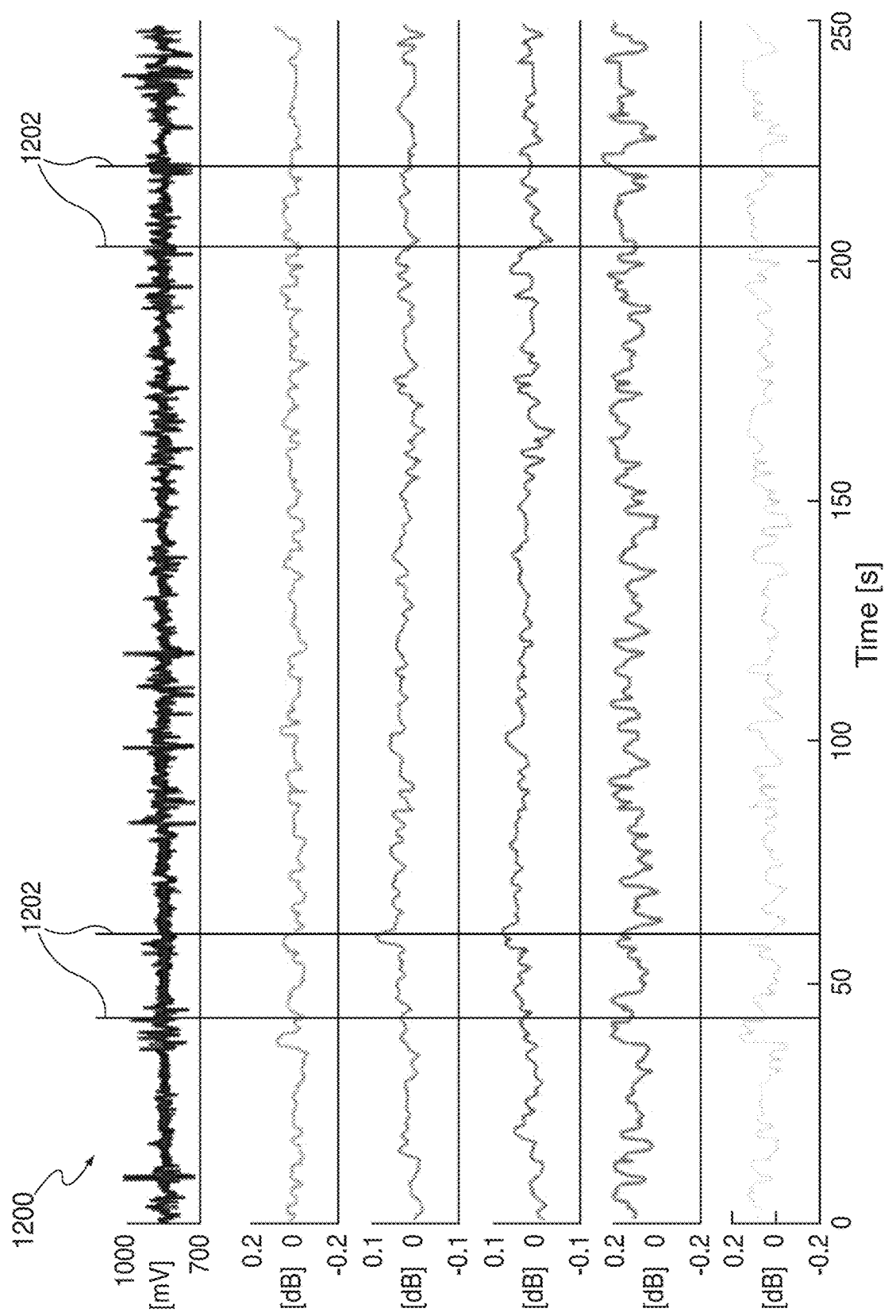
FIG. 12 is an illustrative example of timestamped raw and frequency-processed EEG output.

FIG. 11 is an illustration of use case scenarios uniquely enabled by SCP: process terminating in a perceptual-state prediction application warns user as early as possible that their brain is about to enter an undesirable perceptual state. FIG. 11 represents an experimental setup for unambiguously generating perceptually opposite perceptual states by inducing cold pain. Healthy subjects inserted a hand into 0 degrees Celsius water bath (item 1104) until reaching a self-reported 8 on a 1-10 pain scale (10=insufferable pain). Upon reaching the self-reported 8 level of pain, the subject removes the hand from the bath (item 1102). FIG. 12 shows an example of timestamped raw and frequency-processed EEG output. Timestamps are shown as item 1202.

Results

Self-Calibrating Protocol Using Cold-Induced Pain States

EEG methods have been studied as detectors and quantifiers of pain in patients who are unable to communicate. A similar cold-induced pain vs. no-pain protocol may be used as a surrogate for a generalizable perceptual brain state. This modality benefits from unambiguous external validation by experimenter independent of subject's self-reporting: pain cannot start before subjects insert their hand in the ice bath, and it is clear that pain is high in the moments immediately prior to when subjects remove their hands from the ice bath (FIG. 11).

Machine Learning and Classification

The main focus of the computational analysis was to extract and select features from the EEG signal and apply machine learning techniques to study their applicability to generalized state classification in a low-overhead computational setting, i.e. real-time on tablets and mobiles coupled to wearable wireless headbands. For purposes of illustration, a performance assessment was done for five classification algorithms, ranging from modern techniques such as Supporting Vector Machines and Complex Decision Trees, to classical machine learning algorithms (k-Nearest Neighbors and Perceptron Neural Networks), as they are generally considered well-suited for analysis of stationary EEG signals.

Data Analysis: "Pain" State can be Distinguished from "No Pain" State

Confirmation was made that one could reliably use self-calibrated data to distinguish between two different states. Each subject's data was split into 256 samples windows (90% overlap) and each window was counted as one observation. Observations were split into three classes titled "pain", "no pain" and "unknown" based on the flow of the experiment and the subjects references. The observations prior to inserting the hand into the ice bucket and after the user reference of 'end of pain' were labeled as 'no pain.' The observations sufficiently after the 'start of pain' indication until the hand's removal from the ice were labeled as 'pain'. The rest of the observations were labeled as 'unknown' to be classified as one of the two other classes after the training of the classifiers. For the rest of the analysis, observations from a single subject were used as the training set and the rest of the subjects as a test set. It is a core part of the Self-Calibrating protocol to train based on personal data and not population averages, thus every algorithm was optimized for cross-validation, i.e. splitting train-set into two parts and using one to train and one to test. Yet, a test-set comprising of other person's data is a good measure for the generalization ability of our classification scheme.

Figure 16:
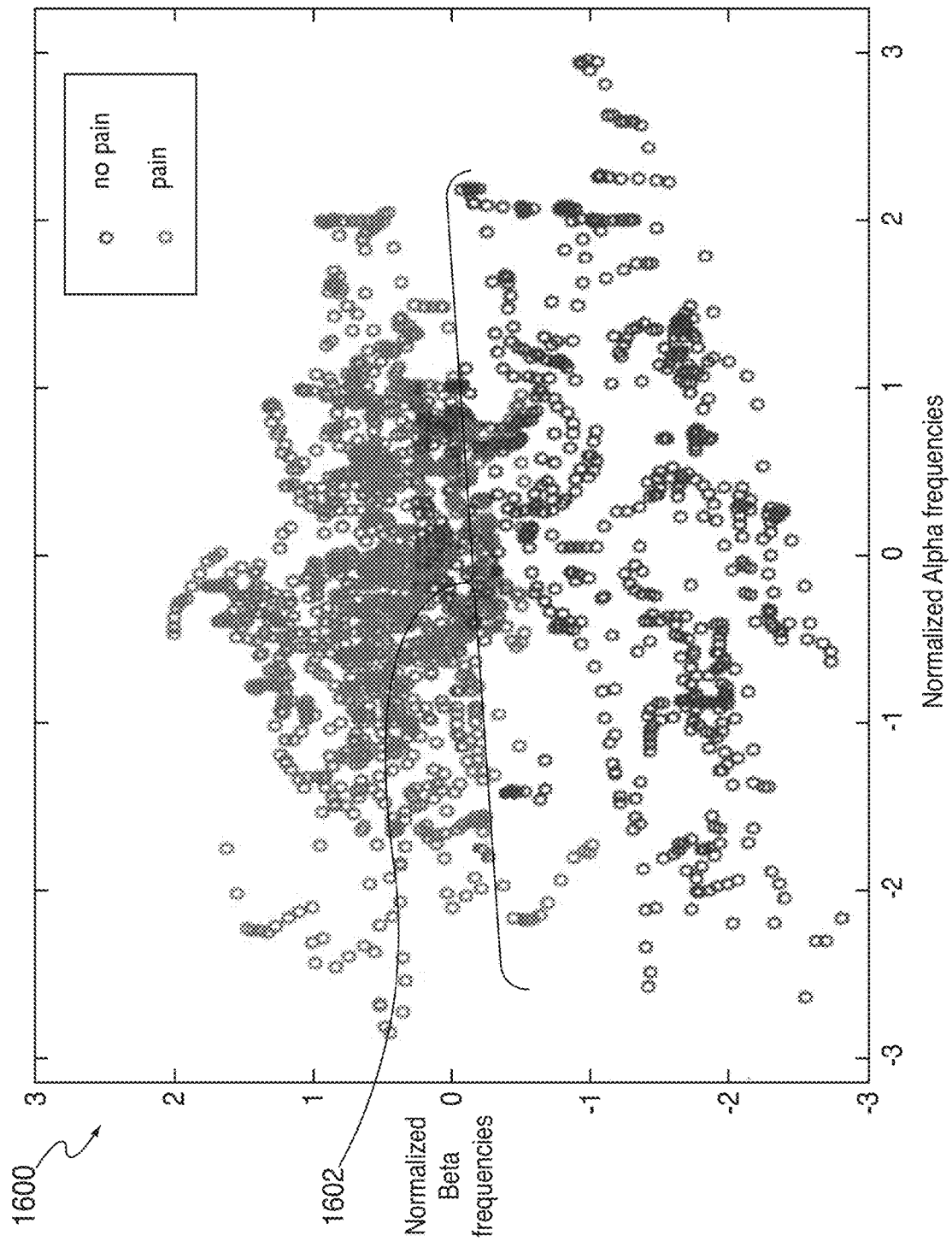
FIG. 16 shows a scatter plot of two features (mean alpha frequencies, mean beta frequencies) indicating that frequency domain analysis can provide sufficient separation between the two classes.

Results from past experiments show evident changes in the frequency content of the EEG signal during acute pain. On the direction of implementing an embedded software for the classification, Fast Fourier Transform is the fastest of all other available methods for frequency analysis in real-time applications. In the case of this trial, a short FFT is performed from the DSP module of the headband every 22 samples, with a window size of 256 samples. Thus a feature vector was able to be constructed with frequency data with a rate of 10 observations per second. The vector comprised a total of 25 features based on the power in the 5 frequency bands ($\theta,\delta,\alpha,\beta,\gamma$) and the location of the sensors (left ear, left forehead, right forehead, right ear). A z-score normalization was performed on the whole set of observations for every feature. FIG. 16 shows how using the SCP for a single subject allows for the clear separation of pain from no-pain states using frequency domain analysis. In this case normalized $\beta$ frequencies tend to be higher in the pain state. Separating hyperplane 1602 shows generally the separation between pain (above) and no pain (below).

Determining the Best Classification Algorithm

Figure 13:
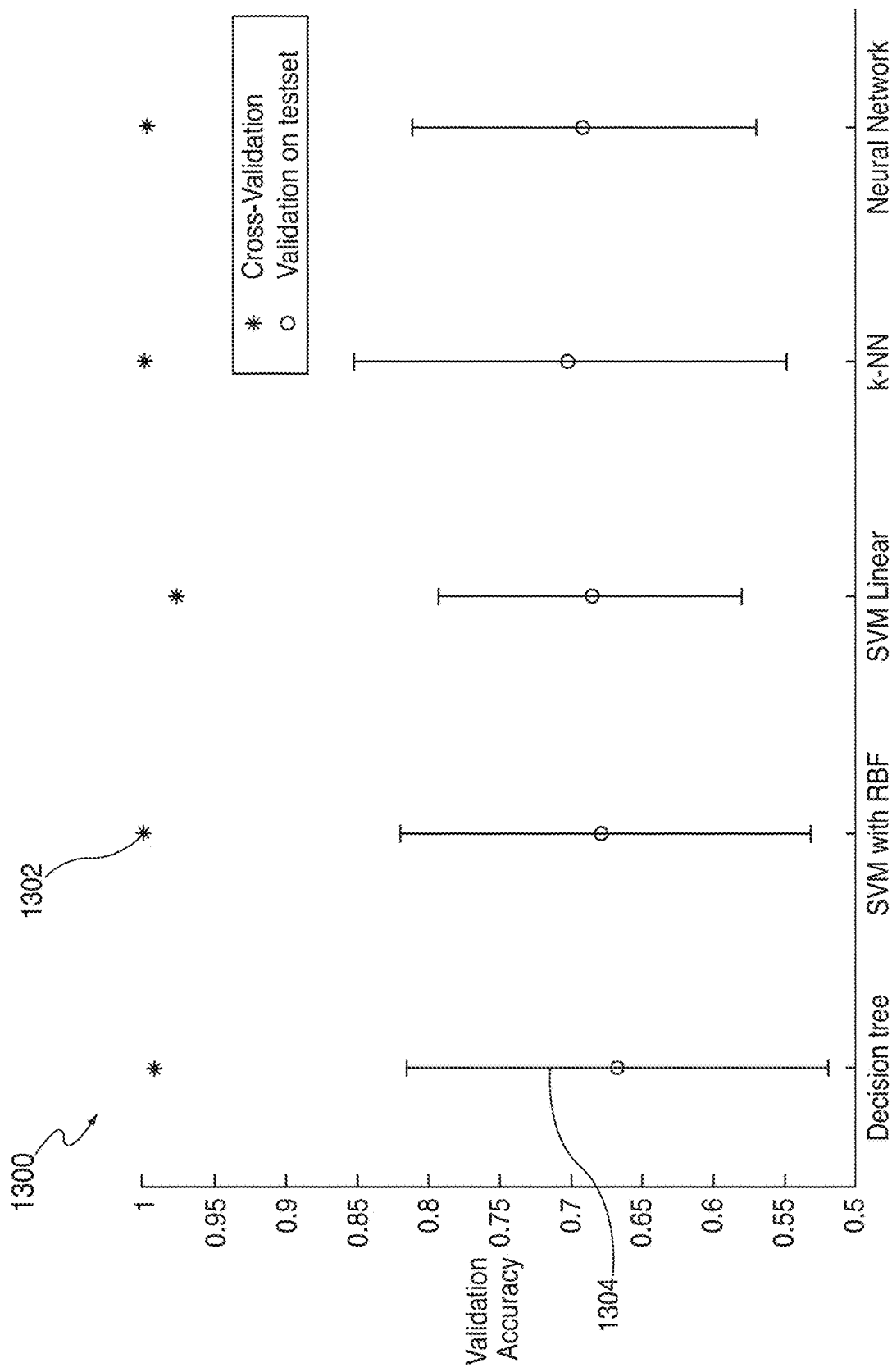
FIG. 13 shows the validation accuracy of 5 different classifiers on pain no pain state differentiation, every algorithm tested with 500 different ensembles of features, error bars indicate maximum and minimum preferences.

Another consideration is the role the classification algorithm may play in reliable analysis of the EEG data in an exemplary SCP. Various classifiers were tested in order to determine which perform better with stationary analysis of EEG data. The candidates were 1) decision trees, 2) supporting vector machines (SVM) both with 3) linear and 4) nonlinear kernels, k-nearest neighbors and a 5) perceptron neural network classifier. Prior to the comparison test, each classifier's parameters were optimized with random sample tests in order to achieve validation accuracy greater than 50%. During the test, each classifier was trained on a "training" dataset, cross-validated with 5 folds and tested on a test set for 500 different ensembles of a random number of features. The resulting comparison of the different classification algorithms was visualized using the cross-validation accuracy (item 1302 of FIG. 13) as well as the average and maximum validation accuracy on the test set (item 1304 of FIG. 13). The characterization concludes that the best performing classification algorithm was the k-Nearest Neighbors (kNN), with a higher average and maximum validation accuracy, although the performance of other classifiers was not far behind (FIG. 13). Thus simple self-calibration protocols such as timestamped data labeling followed by feature extraction and algorithmic parameters play the main role in reliable EEG classification while the choice of the specific algorithm is of secondary importance. This result is consistent with the good separation of the two self-calibrated classes that robustly corresponded to features that could easily be found using frequency domain analysis of the signal.

Optimization of the kNN Algorithm

Figure 14:
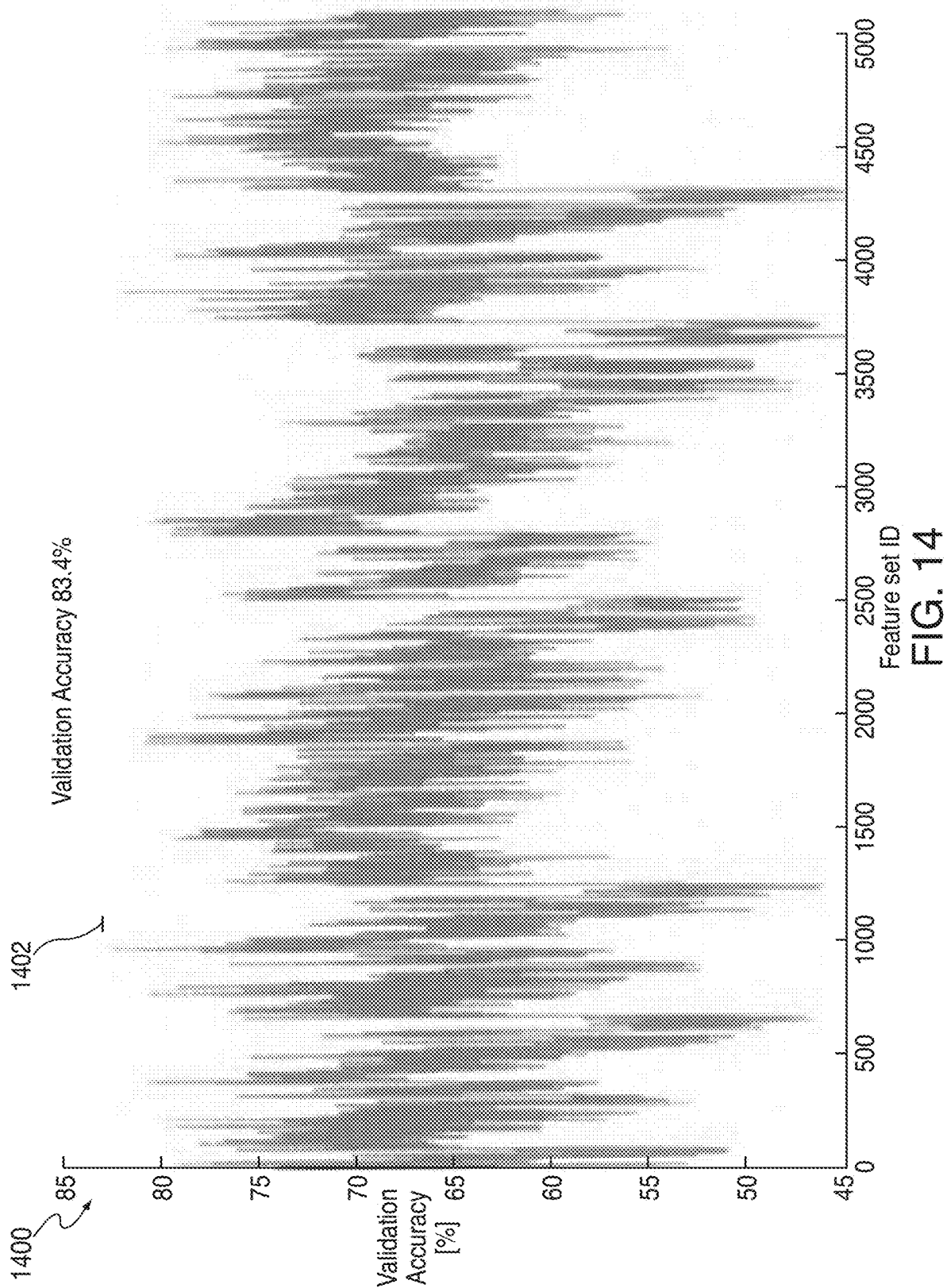
FIG. 14 shows the average validation accuracy of the kNN classifier for 5000 different sets with the optimal size of features, the maximum validation accuracy achieved is 83.4%, when the classifier was tested on a different subject than the one trained.
Figure 15:
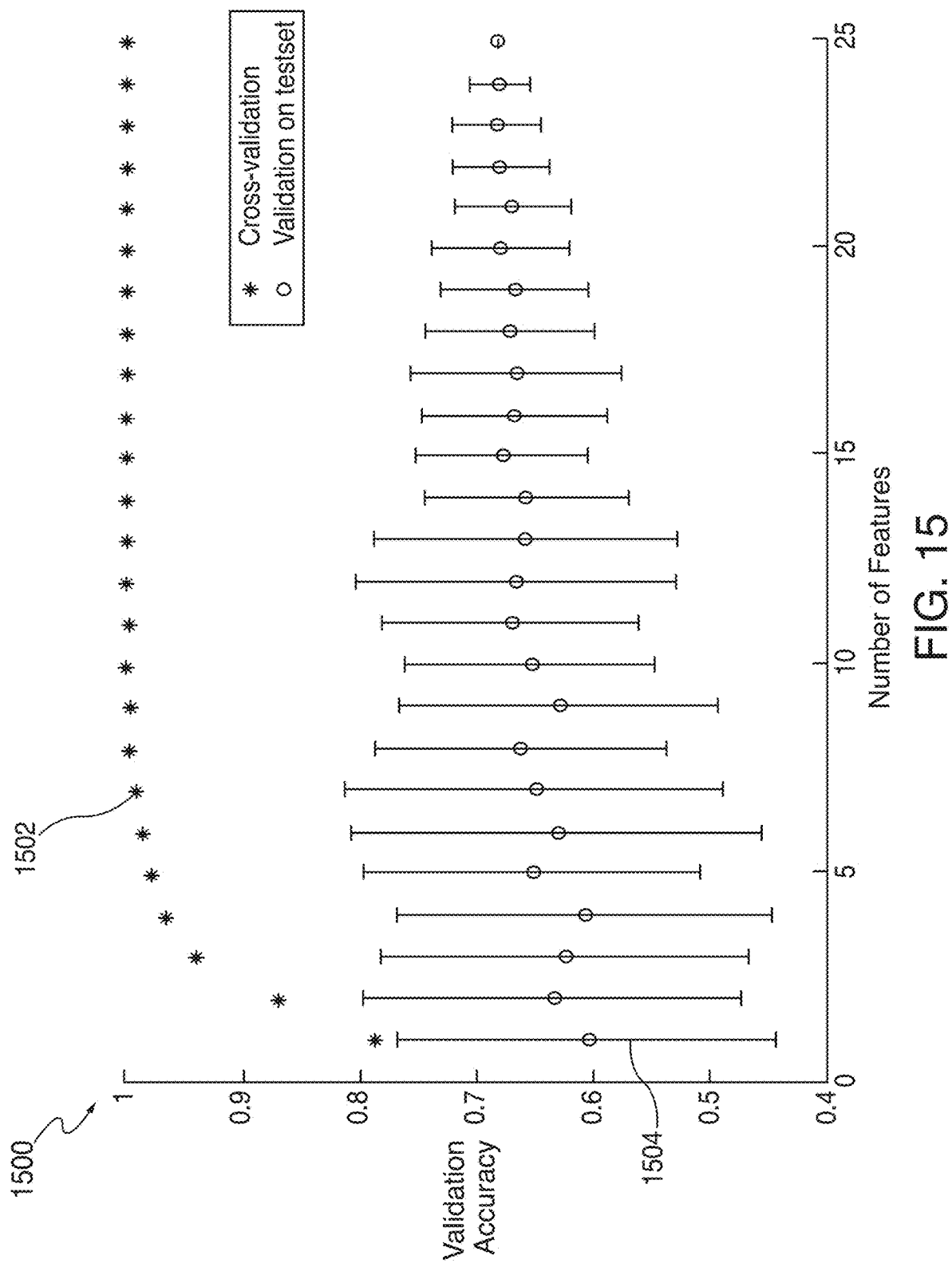
FIG. 15 shows the average validation accuracy of the kNN classifier as a function of the number of features, for every number of features were produced 200 unique sets and their performance was averages, error bars show the range in performance between different training sets.

Subsequently, the performance of the kNN algorithm can be further optimized as a function of the feature vector size and content. In order to assess the size of the feature vector a random sample of 2000 unique feature vectors were generated of every size between 1 and 25 (FIG. 15). It is apparent that for larger feature sets the performance of the classifier converges to the average value (test set) and to a maximum cross-validation accuracy. Yet, with just seven features we can already achieve robust classification performance. The second step of the optimization was to determine which ensemble of seven features performs optimally as the training set. For this step 5000 unique feature sets were created, uniformly distributed through the 480070 possible arrangements (25 choose 7). FIG. 14 shows that the maximum validation accuracy achieved is 83.4% (1402), when the classifier was tested on a different subject than the one trained.

Figure 18:
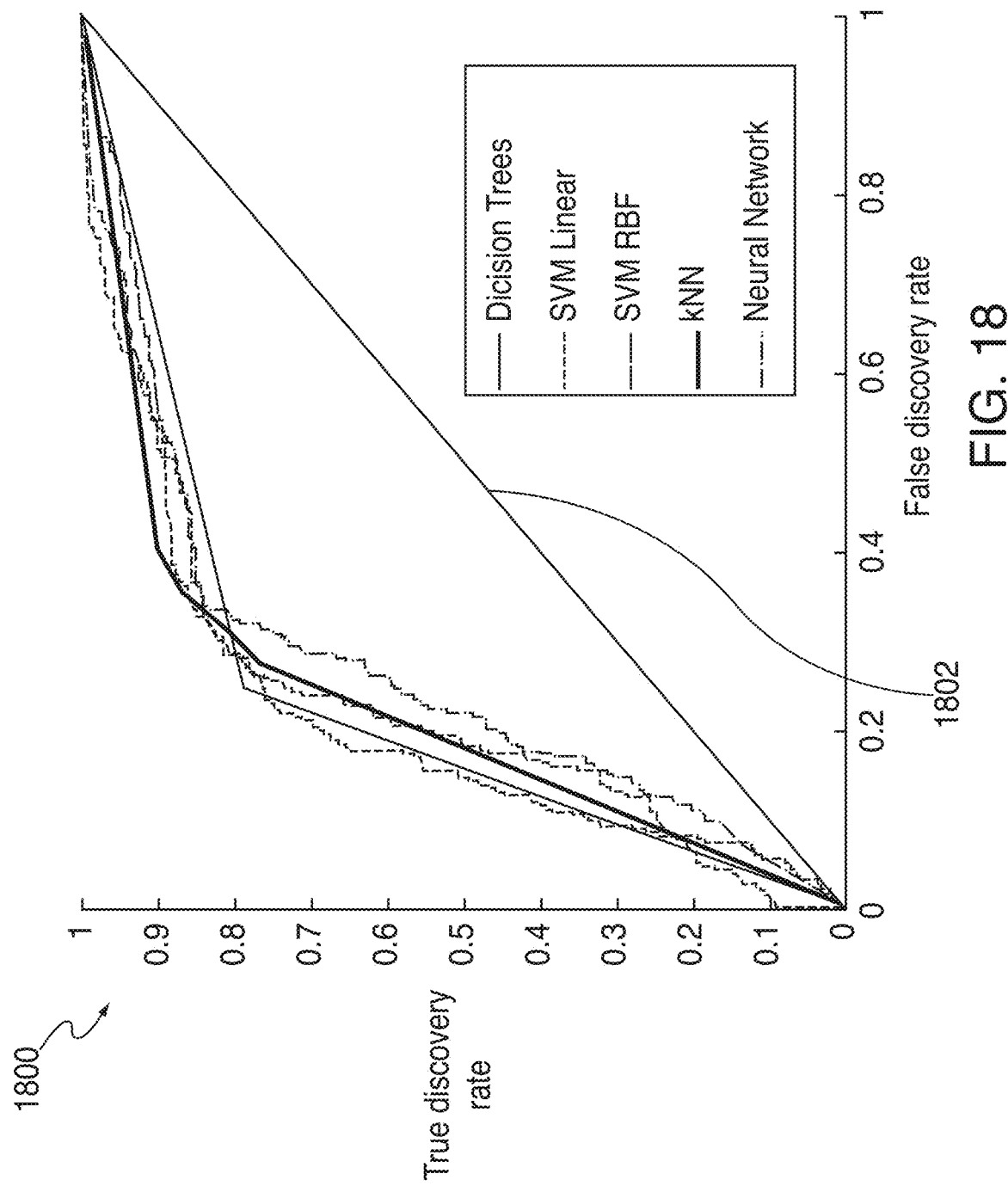
FIG. 18 shows the Receiver Operating Characteristic (ROC) curves for 5 classifiers.

The validation accuracy on the test file for each one of the sets is presented FIG. 15, which tracks the set with the maximum performance. More particularly, FIG. 15 shows the average validation accuracy of the kNN classifier as a function of the number of features, for every number of features were produced 200 unique sets and their performance was averages, error bars show the range in performance between different training sets. FIG. 15 shows cross-validation performance (1502) and testset validation performance (1504). FIG. 18 shows the ROC curves for 5 classifiers, with random classifier 1802.

Application

The present invention represents first steps towards defeating the problems associated with cross-applicability of EEG calibration achieved against a wide average in favor of SCP for NFB in wearable settings. In the U.S., EEG sensors are currently considered class II medical devices, and applications for clinical use are FDA-regulated, requiring a 510K registration (marketed only to certified medical providers). The only FDA approved indication for neurofeedback currently is relaxation. One major obstacle to the goal of moving EEG from the clinician's office to an at-home efficacious treatment and brain training tool is the practice of using a normative database to focus neurofeedback targets. The main requirement for inclusion in a normed database is general health. The argument for using such databases rests on the problematic assumption that there is a "healthy normal" that is invariant in a particular age group.

However, there is vast inter-individual variability in EEG as well as significant intra-individual variability over time-especially important in the case of training that is actually effective results of which should be reflected as a progressive movement of baseline brainwave patterns over repeated sessions. In direct response to this effort, computational methods decouple any particular brain region or putative physiological mechanism from the application of neurofeedback as a brain training tool, allowing the patient/client/home-user to assign arbitrary experiences to perceptual states generically designated as "up" and "down" and train for one against the other.

The end goal of this invention is to create a versatile and reliable platform for EEG neurofeedback unlimited by the availability of well-characterized neurophysiological states obtained from calibration to other users. Without loss of generality, for experimental convenience and to obtain a robust and unambiguous data set including generalizable "up" and "down" states a well-studied industry-standard pain/no-pain protocol was used involving the immersion of one hand into an ice water bath to quickly and reversibly induce pain that transitions from barely noticeable to unbearable within tens of seconds.

Using this protocol, results demonstrated that it is possible to reliably and robustly distinguish the "pain" and "no pain" states in a self-calibrated manner. Five algorithms were used to determine which gave the best validation accuracy and found that although the k-NN algorithm performed the best, but the choice of algorithm is secondary to the choice of features. A number and specific set of features necessary to optimize the k-NN algorithm (or any algorithm) can be characterized. Any type of classification algorithm could be optimized based on a number and specific set of features.

Upon generalization of these methods, a typical embodiment would be a headband EEG sensor wirelessly transmitting processed data to the visualization and UI platform. Currently, these are in the form of a personal computer, tablet or smartphone that run additional signal processing, machine learning and user feedback interface and handles historical data storage. Optionally, (historical) data storage and analysis could take place off-platform in the cloud allowing identification of trends and detection of new correlations over individuals and populations. Such embodiments may optionally integrate functionality of other wireless sensors such as heart rate, blood pressure, generalized activity as conferred by accelerometers, blood sugar and, more recently the always-on bio-compatible flex circuitry. In the latter case electrodes are embedded in conducting polydimethylsiloxane (PDMS) elastomer which upon doping with carbon black makes a surprisingly robust and comfortable skin contact electrode Additionally, EEG has long been used in clinical settings to evaluate neurological disorders and has been proven useful even in wearable settings (e.g. predicting seizures and strokes. Further empowering EEG as a diagnostic tool when available for at home-use is the capability of continuous monitoring. Several seemingly unconnected physiological actions such as maceration and blinking (easily tracked by EEG) are known to undergo long term changes that can be used in diagnosing early stage neurological disorders such as Parkinson's and Alzheimer's, providing differential diagnosis of epilepsy and distinguishing among various causes of altered cognition (for example, encephalopathy vs. dementia). Such monitoring is impractical in a clinician's office due to the requirement of prolonged data collection, but would become practical in a wearable, at-home setting.

While these medical and performance enhancement application directions are impacted by the present invention, the scope of this invention shows that using an off-the-shelf, inexpensive (under $300 USD retail) wearable EEG sensor, with modest computational overhead, useful features can be automatically learned and extracted by the application of the herein disclosed Self-Calibrating Protocols coupled to standard machine learning algorithms.

Accordingly, SCP applied to EEG in neurofeedback training or predictive mode empowers off-the-shelf consumer grade wearable EEG sensors with new capabilities. While herein is discussed a Muse headband EEG sensor, the results are widely applicable to current and future inexpensive wearable EEG sensors (and future MEG and other hybrid multimode EEG/MEG/Heart Rate/Blood Pressure/Blood Sugar/activity etc. integrated sensors that are currently being developed for the iPhone and iWatch and similar). The onboard signal processing capabilities of these continue to grow more powerful as the sensing becomes more robust and feature extraction faster and more reliable. The visualization systems are currently limited to PCs, tablets and smartphones but can eventually be ported to smart-watches and eyeglass displays. The machine learning and user feedback interface can be iteratively optimized as historical data storage and analysis would take place both on-platform and in the cloud allowing for the identification of trends and detection of new correlations. Additional to enhanced consumer grade applications, EEG sensing that has long been used in clinical settings to evaluate neurological disorders (e.g. predicting seizures and strokes, early diagnosis of neurodegenerative diseases etc.) can be enhanced when moved from the clinician's office to the user's home and worn continuously. The potential of wearable, adaptive dynamic EEG as a powerful diagnostic tool is enhanced by applying the SCP principle even without the NFB functionality.

Additional Discussion

Without being limited by theory, the various kinds of "perceptual state(s)" and "perceptual state opposites" are general concepts defined here by their characteristics as loose analogies to intuitive example cases.

(1) "Rankable" Perceptual States with "No Unique Opposites"

Perceptual states that can be unambiguously ranked by type and intensity (e.g. pain, itch, hunger) but whose "opposites" do not correspond to any particular perceptual state are of significance to the applications of this invention.

These cases typically correspond to many qualitatively and quantitatively distinguishable perceptual states associated with a well-defined sensation type and smoothly varying sensation intensity (they are linearly "rankable" and can be unambiguously ordered on a scale smoothly varying from low to high intensity with any number of steps between the extrema. The extrema are defined as "no sensation" at the low end and "highest intensity experienced so far". The high extremum is therefore experience-dependent while the low end is fixed, independent of experience.

By definition these kinds of perceptual states have as their common "opposite" any perceptual state where the intensity of the sensation is zero. Example: the perceptual state corresponding to the sensation pain resulting from submerging one's hand in ice water. The "perceptual opposite" of this state is not the sensation resulting from submerging one's hand in hot water.

Crucially important to many of the applications enabled by this invention is the correct assignment of opposites. Specifically: NFB training towards "hot pain" will not decrease the perception of "cold pain". Instead, NFB training to modulate pain perception is achieved training towards any no-pain state by rewarding time spent out of "pain" state by tuning the threshold dynamically (see 2 below) as pain perception is decreased.

(2) Dynamic Tuning of Threshold:

The hyperplanes described in FIGS. 806a and 806b and 1602 can be used as "dynamically tunable thresholds" to achieve a directional arrow during NFB reward that points towards the direction corresponding to being "out of pain" by rewarding a highly mobile perceptual state. This is loosely analogous to rewarding the brain to divert attention from pain without asking it to focus attention on any particular other thing let alone try to do the impossible and "stop thinking about pain". Instead NFB encourages to defocus from the pain sensation without referencing the sensation itself.

While a traditional approach would be to have the NFB reward being scored by time spent below the hyperplane (corresponding to "no pain of this type") this approach asks the brain to somehow enter a well-defined perceptual state from being in its opposite and this requires recalling a specific memorized perceptual state and attempting to enter it without presenting any NFB reward for incremental movements away from "pain" in any direction.

What is worse, it overburdens the user by requiring they enter a specific state while in fact any other perceptual state that happens to have low or zero pain intensity will be easier to achieve and a perfectly acceptable outcome that can then be recorded and used as to reward reinforcer.

The first problem the dynamically tuneable threshold approach solves is it allows to defocus from a state without referencing the state (which brings the sensation back to the forefront of attention).

The second problem the dynamically tuneable threshold approach solves is it increases the chances of finding a true "no pain state" by exploring many states since movement is encouraged. Even if movement towards the recorded opposite is hampered, a new "desired state direction" appears as the threshold changes in shape and size from being a circle centered on the first perceptual state (which of course corresponds to pain) meaning that transition to literally any state is rewarded. At the next step the threshold is adjusted such that the probability of a random transition that moves away from high density clusterings of pain states is rewarded and so on. Even while still in pain territory, NFB can be scheduled to enter a forced refining cycle and ask the user "your pain appears to have started decreasing over the last moments, could you confirm?" assuming there is no physiological source causing additional pain, the user will be by definition momentarily distracted, having to perform a task which while it does explicitly reference pain, also strongly suggests that the perceived intensity has decreased.

Even if the user was experiencing an identical level of pain the strong preference towards positive response is at the very least a placebo-like encouragement to keep at the NFB exercise while the best case scenario is a self-fulfilling prophecy that is detected as randomly entering a no-pain state in the next cycle.

Such an even is bound to happen eventually and as soon as such a state has been discovered and experienced even momentarily, the user is notified by the visual cue of not just earning points for searching but earning a tier-1 "achievement reward" letting them know they have managed to enter a no-pain state however briefly. In addition to proving to the user that the task of escaping pain perception is within their reach, with the first "achievement award" marking a moment fresh in memory, the brain has an easier time responding to the NFB reward and returning to a just experienced state. Crucially, the platform now has a record of an actual specific state towards which it will now motivate by dynamically tuning the threshold again. While points are still rewarded to move around while in pain states, every time perception state re-enters the newly discovered or any other no-pain state an achievement award is given and while points for moving accumulate faster while out of desired state, entering a no-pain state gives a tier1 achievement award, staying in a no pain state for double the number of seconds user stayed in it the last time earns the a "tier2 mastery award" (see below).

This scheme incentivizes the user on many levels corresponding to the various types of hard work they are accomplishing.

To this end, the dynamically tuneable threshold acts effectively as an incremental "guide" always pointing out of the pain state by rewarding movement and searching around states, instead of the much harder to incentivized directed movement toward "the opposite".

This is done by keeping the classifier function intact but once the hyperplanes have been established, they are set artificially high, meaning that during the start of NFB pain reduction even in the presence of pain sensation as self-reported and/or EEG detected, the feedback starts rewarding points at a variable rate. The rate is never zero but the accumulation of points slows down as the user's perceptual state remains "stationary" and the rate of reward increases as the user's state "moves around". Here a state is defined as being stationary if it crosses the dynamically tuned rarely, and defined as "moving around" when threshold crossings are frequent. In order to force threshold-crossing events to appear, the hyperplane is set artificially high corresponding to any state detected in the next interval will count as having crossed the threshold unless the next state is the exact same as the current state.

This is necessary because the perceptual opposite of pain due to cold is simply "no pain"-corresponding to lack of pain perception and it is perceptually the same for lack of all kinds of pain. In other words, the perceptual state of "no pain" is not considered a stand-alone perceptual state as it is only defined as the lack of perception by reference to experiences stored in memory. While there are many types of pain and their intensities can be modulated, from the standpoint of "perceptual state opposites" all types and intensities of pain have the same opposite: "no pain." Belaboring for the sake of an intuitive understanding of this situation: this case is loosely analogous to the case of "black" when defined as the complete absence of light. Black has no wavelength or intensity, and is not the perceptual or physical opposite of "white" or any other color. Black is however the common "endpoint" state for all color perceptional states when the stimulus intensity (strictly "flux here") is decreased to zero photons per unit time per unit area.

Example NFB Reward Scheme Leveraging Tunable Thresholding:

Trickle points: constant rate of points per second when EEG is being measured recognizing effort involved in just getting started and keeping electrodes in contact.

Searcher points: double the rate for every threshold crossing for half the time of previous stationary state, i.e. if pain state X is detected for 6 seconds, crossing into pain state Y doubles the rate for 3 seconds, rate return base trickle point rate, state Y is now re-arranged in the map as being "close" to state X by virtue of being the temporally closest during the search. Re-entering state X directly from state Y is rewarded identically to the first threshold crossing (since it does correspond to a transition in both state and direction). After both states have been visited from each other they are to be "merged" and additional transitions among them do not earn threshold crossing points. The rest of the strategy is similar resulting in growing islands of states that are considered close, internal re-arrangements of distance are not relevant at this point since an ergodic path taking place by hoping from pain state to other pain state results in motivation towards more exploratory movement.

Discovering new pain states is thus rewarded because it motivates search but staying in them is not as they gradually merge into one state.

First instance of entering a no-pain state is rewarded by an attention-grabbing "tier 1 achievement award" and a large jump (boost) by a chunk of points, e.g. if the trickle rate is 1 point per second, finding the first no pain state pays 1000 points in addition to the achievement award.

Discovering additional no pain states by transitioning from a no pain state results in achievement awards but no boost, leaving no pain state to enter a known or unknown pain state defaults back to threshold crossing rewards, returning to a known no pain state from any pain state results in achievement award and boost, staying in a no-pain state for a period of time 50% longer than the previous record is rewarded with a "mastery tier 2" award.

Once a true no pain state is detected, NFB can enter a refining phase to a bubble encompassing the area containing the most no pain states of the first to find the perceptual state.

The above are driven towards using traditional NFB rewarding (i.e. reward points at most rate for relative time spent in "no pain"-specifically each visit to no pain earns points at a rate that is faster than the rate for each threshold crossing and intermediate reward milestones are therefore more likely to be rewarded while in no pain state instead of while moving around pain and no pain states.

(3) Non-Rankable Binary Perceptual States

These are perceptual states that are experienced during active task performance as either being "on" or "off", the transitions being reported as "abrupt" as opposed to gradual. These states cannot be ranked by "intensity" instead they can be broadly classified by the percent of time spent in one of them during task performance. Additionally, the total number and temporal pattern of transitions between states is a useful measure that can be tracked, correlated with task performance and used in aid of extracting sets of classifier handles for self-calibration, sensing, and NFB training.

Example: the experience of being "in the flow" [REF Csikszentmihalyi, Mihaly (1990). *Flow: the psychology of optimal experience* (1st ed.). New York: Harper & Row. ISBN 9780060162535.] with its opposite being "out of the flow". These are examples of what are defined as "non-rankable binary perceptual opposites" and for the purposes are here defined to have a meaning loosely similar to the colloquial expression of someone being "on their game" or "off their game," corresponding to "high vs low performance" (as self-described and optionally independently verified) during physical and/or mentally demanding tasks.

Without loss of generality, familiar examples of non-rankable perceptually opposite binary states that are robustly tied to significant changes in outcome can be: training/playing sports, trading, coding, calculating, inventing, brainstorming, piloting, driving, performing and composing music, improvising, rhyming, acting, singing, writing, reading, painting, sculpting, learning, memorizing, live translating. Such tasks are widely understood to have measurably different qualitative and quantitative outcomes predictive of whether performer will report they were "in" or "out" of their "flow" while performing the task (universally, performance is higher when task is performed with a high percentage of time being in the flow than out). Flow is sometimes described as the feeling of being "in tune" with one's body and mind and/or having "effortless mastery" over body movements and mental constructs. It can also be experienced by one or more of a group working together, and is characterized by achieving seamless communication and orchestrated behavior. Examples include performing as a coherent sports team, or as a member of music ensemble or flight crew. This perceptual state can be independently tracked, not only as evidenced by better outcomes at the end of the task but also as a spike in efficiency and timing in the use of instruments and complex machinery, reaching theoretical performance limits.

(4) Rankable Perceptual States with Unique Opposites

Some perceptual states are readily rankable in their intensity and have opposites that are robustly defined. For instance the experience of being "anxious" has the unique perceptual opposite we call "calm". One cannot find themselves in a state that is simultaneously perceived as being anxious and calm (although there are conditions that cause subjects to experience rapid fluctuations between the two perceptual states. Generally, we can track and unambiguously rank the transition from being "very anxious" to "a little anxious" to "mostly calm" to "totally calm" and the number of steps that can be defined in between the extrema are a matter of desired resolution and practicality. Another example of a rankable perceptual state with a unique opposite is "alert" whose unambiguous unique perceptual opposite is "foggy" (sometimes referred to as "sluggish" or "lethargic"). As with "pain" vs "no pain" and "in flow" vs "out of flow" the "desirable" state in such cases is almost always self-evident and task-independent (i.e. tasks where performance is improved when a person is "anxious," "foggy" and "in pain" as opposed to "calm", "alert" and in "no pain" are rare). EEG-based alerting to warn user they are entering an undesirable state is of obvious utility here as is the application of NFB training towards returning to the desired state.

(5) Rankable Perceptual States with Non-Binary Perceptual Opposites

Note the case of attention that can "focused" vs "diffuse" vs "hyperfocused", as an example of "non-binary perceptual opposites" where the "desirable" state in each pair is heavily task dependent. Any set of two chosen from these three makes for unambiguous "perceptually opposite" states a user may report as experiencing during performance of a task and each of the three can be the desirable or undesirable of a pair depending on nature of task (e.g. when flying under instrument conditions the pilot's performance is best when attention is "diffuse," while during landing pilot performance is best when attention is "focused," and when the pilot is performing navigational computation "hyperfocused" leads to fewer mathematical errors.).

Note the task itself may be directly designed to induce a perceptual state: such as guided meditation designed to induce calmness, or neurofeedback gaming designed to enhance focus, as is routinely done by EEG practitioners when treating anxiety or ADD in clinical settings.

(6) Summary Generalized Use Cases

In the exemplary implementations of this invention, the same EEG sensor operating under different settings may be used to learn to track, report and trigger on multiple "perceptual opposites". This means that, within limits, the same sensor can be biased to increase resolution of detection by dynamically changing its affinity and response to perceptual states deemed more salient at any time by the user themselves, or by automated scheduler that is triggered by parameters such as time elapsed since last transition. Such dynamic adjustment to schedulers can be triggered by signals from other sensors on the user, including accelerometers mounted on the same headband as the EEG sensors that may detect activity, temperature, posture, etc. Triggering may be from signals collected by other sensors detecting work by the user or present in the immediate environment. Triggering may also be from external sources, reporting for instance changes in ambient environment, for example from "internet of things" devices such as thermostats, or machine olfactors. Triggering could also be from data optionally being collected from the internet such as for instance changes in local weather or stock market conditions.

Without loss of generality, in all use scenarios including cases of NFB training and during refinement, both raw and processed EEG signal traces as well as any number of external data streams, including but not limited to performance metrics such as for instance trading or gaming performance, eye tracking, key and cursor logging, or self-administration of analgesic, and physiological metrics such as blood pressure, heart rate, galvanic skin response, as well as social metrics such as tone and content of emails, written or customer service interactions, can be time-stamped and stored alongside the EEG signals to be used for correlation extraction for personalized use and refinement of machine learning, or aggregated over individuals for data mining and performance enhancement of algorithms, predictors, and schedulers for diagnostic and therapeutic NFB applications, as well as marketing research.

(7) Generalizable to Wearable and Non Wearable, Local and Remote Additional Sensors, Processors and Platforms In exemplary implementations of this invention, one or more computer processors are specially adapted: (1) to control the operation of hardware components of the EEG sensor array, including electronic circuitry, electronic sensors, accelerometers, schedulers, onboard signal processors, bidirectional communication with external sensors and actuators including but not limited to LAN, WAN or internet-connected PCs, tablets, smartphones as well as thermostats, light dimmers, cameras, microphones, valves and pumps; (2) to perform computations for pattern recognition and perceptual state matching; (3) to receive signals, including signals indicative of sensor readings or human input, or over the internet corresponding to data streams collected from wearable or other sensors operating locally in direct contact with user or another user or remotely (4) to output control signals, including control signals for controlling modulation of EEG signal processing, providing extra features to machine learning algorithms and classifiers and control signals for controlling transducers to output information in human perceivable format, and (5) to process and record data, perform computations, and control the read/write of time-stamped, annotated data to and from memory devices. The one or more processors may be located in any position or positions within or outside of a wearable EEG sensor and the PC/phone or tablet to which it is primarily connected. For example: (1) at least some of the one or more processors may be embedded within or housed together with other components of a wearable EEG headband, such as the sensing electrodes or their associated electronic boards. Processing may also take place on a non-dedicated processor such as that present in a smartphone/tablet or PC or on more than one processor each embedded in a same or different type of device using same or different software (2) at least some of the one or more processors may be remote from other components of the device. The one or more processors may be connected to each other or to other hardware components in the EEG sensor and the User Interface and Neurofeedback Platform [item 110 of FIG. 1]: (1) wirelessly, (2) by wired connection, or (3) by a combination of wired and wireless connections.

Generalizable to Multiple EEG Sensors Optionally Coupled to Other Sensing Modalities This invention may be implemented as a method comprising, in combination: (a) measuring test responses, the test responses comprising EEG data collected by EEG sensors during under multiple testing conditions during self-calibration runs of one or more perceptual states; (b) using one or more processors to compare (i) the test responses and (ii) recorded responses of a second set of EEG sensors to one or more positive controls under the multiple testing conditions; and (c) using one or more processors to determine whether or not perceptual state conferred by the test matches perceptual state conferred by all or some of the one or more positive controls.

Furthermore:

(1) the first, second and third sets of sensors may each be calibrated to respond orthogonally or semi-orthogonally to the positive control perceptual state;

(2) (i) the first and second sets of sensors may each be arranged "in series" (i.e. by placing a second sensor to record a second calibration protocol in the same manner the first sensor was calibrated—from the same parts of the scalp) or "in parallel" (i.e. by placing a second sensor to record at the same time as the first sensor but from different parts of the scalp), (ii) the method may further comprise using at least one processor to output control signals to make an adjustment to a second sensor, which adjustment is based at least in part on output from the prior sensor, (iii) the adjustment may comprise an adjustment to the signal processing parameters such as FFT window size, sampling rate, pain thresholds the classification algorithm parameters such as learning rate, weights, number of nearest neighbors and any of the other parameters affecting calibration, refinement and NFB phases; and (iv) the "first" and "subsequent" sensors may each refer to the signal of actual electrodes physically present in the same or different headband, or may each be sensors of additional modalities including but not limited to measurements such as Galvanic Skin Response, heart rate (plethysmography), blood pressure, blood oxygenation, blood sugar, eye tracking, thermography, body temperature (including Forward Looking Infrared images of face, functional Magnetic Resonance Imaging or Positron Emission Tomography of brain or other tissues) and others.

Generalizing to Series and Parallel Operations

This invention may be implemented as apparatus comprising, in combination: (a) n sets of EEG sensors, wherein each of the sets of EEG sensors (i) are calibrated (or are adapted to be calibrated) to respond orthogonally or semi-orthogonally to a positive control perceptual state and (ii) are arranged in series; (b) one or more processors controlling how a signal from a specific set of sensors, out of the n sets of EEG and optionally other modality sensors, is used and processed affecting subsequent use and processing of signals detected including more than one time through the specific set of sensors; and (c) one or more processors for (i) outputting control signals to n-wise modulate one or more groups of sensors, each of the one or more groups including at least one sensor from each of the n sets of sensors; and (ii) determining whether or not a perceptual state conferred during a test run matches a perceptual state conferred by the positive control. Furthermore: (1) (i) a particular set of sensors, out of the n sets of sensors may include a prior sensor and a subsequent sensor, and may be configured such the one or more processors may be adapted to output control signals to make an adjustment to the subsequent sensor, which adjustment is based at least in part on output from the prior sensor and comprises an adjustment to a threshold value, sampling window, feature/handle extraction, scoring functions and other parameters used to tune machine learning algorithms as well as NFB output including timing of warning/alert/refinement events and scoring of user performance electric and (2) the apparatus may further comprise a plurality of ambient environment sensors collecting data such as noise, light, temperature, pressure, relative humidity, gas sensors, machine olfactor sensors (quantifying odor character and odor intensity), as well as performance characterizers such as key-loggers (e.g. measuring typing performance), body position sensors (measuring posture and activity) positioned such that generalized "performance" metrics can be correlated with external parameters that can optionally be slaved to the user's specifications to respond dynamically to changes in perceptual state. For instance, if perceptual state is detected to start a drift from alertness to anxiety, lights, white noise or scent generators may be adjusted automatically in an attempt to nudge user back towards the desired perceptual state. Similarly, this process can be used to discover and self-calibrate personalized ambient environmental conditions that enhance generalized "performance" at any user specified task.

While exemplary implementations are disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention. Numerous modifications may be made by one of ordinary skill in the art without departing from the scope of the invention.

While the above specification and examples provide a description of the invention, many embodiments of the invention can be made without departing from the spirit and scope of the invention. It is to be understood that the foregoing embodiments are provided as illustrative only, and does not limit or define the scope of the invention. Various other embodiments are also within the scope of the claims.

APPENDIX I—EXAMPLE CLASSIFIER CODE

```
function [cvalAccu, tvalAccu, ROC_class] =
run_classifiers(trainset,testset,T_test,predictorNames)
    % This function trains a variety of classifiers and reports back
    % cross-validation and test results.
        predictors = trainset{:,predictorNames};
        response = trainset.label;
        % Train classifiers
        % Perform cross-validation (10-folds by default)
        % Compute cross-validation accuracy
        % Compute accuracy on test file
        TREEClassifier = fitctree(predictors, response, ...
                    'AlgorithmForCategorical', 'PCA', ...
                    'PredictorNames', predictorNames, ...
                    'ResponseName', 'label', ...
                    'ClassNames', {'no pain' 'pain'});
        TREEcrossed = crossval(TREEClassifier,'Kfold',5);
        cvalAccu(1) = 1 - kfoldLoss(TREEcrossed, 'LossFun',
'ClassifError');
        [~,scores] = predict(TREEClassifier,testset{:,predictorNames});
        tvalAccu(1) = 100*(1-confusion(T_test,scores'));
        [X_roc1, Y_roc1] =
perfcurve(testset.label,scores(:,2)','pain');
        clear TREEClassifier;
        clear TREECrossed;
        SVMRBFClassifier = fitcsvm(predictors, response, ...
                    'KernelFunction','rbf', ...
                    'PolynomialOrder', [ ], ...
                    'KernelScale', 'auto', ...
                    'BoxConstraint', 1, ...
                    'PredictorNames', predictorNames, ...
                    'ResponseName', 'label', ...
                    'ClassNames', {'no pain' 'pain'});
        SVMRBFcrossed = crossval(SVMRBFClassifier,'Kfold',5);
        cvalAccu(2) = 1 - kfoldLoss(SVMRBFcrossed, 'LossFun',
'ClassifError');
        [~,scores] =
predict(SVMRBFClassifier,testset{:,predictorNames});
        tvalAccu(2) = 100*(1-confusion(T_test,scores'));
        [X_roc2, Y_roc2] =
perfcurve(testset.label,scores(:,2)','pain');
        clear SVMRBFClassifier;
        clear SVMRBFCrossed;
        SVMLINClassifier = fitcsvm(predictors, response, ...
                    'KernelFunction','linear', ...
                    'PolynomialOrder', [ ], ...
                    'KernelScale', 'auto', ...
                    'BoxConstraint', 1, ...
                    'PredictorName', predictorNames, ...
                    'ResponseName', 'label', ...
                    'ClassName', {'no pain' 'pain'});
        SVMLINcrossed = crossval(SVMLINClassifier,'Kfold',5);
        cvalAccu(3) = 1 - kfoldLoss(SVMLINcrossed, 'LossFun',
'ClassifError');
        [~,scores] =
predict(SVMLINClassifier,testset{:,predictorNames});
        tvalAccu(3) = 100*(1-confusion(T_test,scores'));
        [X_roc3, Y_roc3] =
perfcurve(testset.label,scores(:,2)','pain');
        clear SVMLINClassifier;
        clear SVMLINCrossed;
        kNNClassifier = fitcknn(predictors, response, ...
                    'NumNeighbors',5, ...
                    'NSMethod','exhaustive', ...
                    'Distance','minkowski', ...
                    'PredictorNames', predictorNames, ...
                    'ResponseName', 'label', ...
                    'ClassNames', {'no pain' 'pain'});
        kNNcrossed = crossval(kNNClassifier,'Kfold',5);
        cvalAccu(4) = 1 - kfoldLoss(kNNcrossed, 'LossFun',
'ClassifError');
        [~,scores] = predict(kNNClassifier,testset{:,predictorNames});
        tvalAccu(4) = 100*(1-confusion(T_test,scores'));
        [X_roc4, Y_roc4] =
perfcurve(testset.label,scores(:,2)','pain');
        clear kNNClassifier;
        clear kNNcrossed;
        ROC_class = {[X_roc1 Y_roc1],[X_roc2 Y_roc2],[X_roc3
Y_roc3],[X_roc4 Y_roc4]};
%           RBOClassifier = fitensemble(predictors, response, ...
%                       'RobustBoost',300,...
%                       'Tree','RobustErrorGoal',0.01, ...
%                       'PredictorNames', predictorNames, ...
%                       'ResponseName', 'label', ...
%                       'ClassNames', {'no pain' 'pain'});
%           RBOcrossed = crossval(RBOclassifier);
%           cvalAccu(5) = 1 - kfoldLoss(RBOcrossed, 'LossFun',
'ClassifError');
%           tvalAccu(5) =
sum(strcmp(test.label,predict(RBOClassifier,test{:,predictorNames})))/size
(test,1);
%
%           clear RBOClassifier;
%           clear RBOCrossed;
end
```

APPENDIX II—EXAMPLE DATA LABELING CODE

```
% This script acts on the .mat files directory and updates the database
% of annotated (labeled) data for the pain experiment. The data are
%labeled using the markers as flagposts. Use seperately 3110 and 2501
%files.
% List of files already included in the database:
clear;
clc;
load('andreas_pain_2501');
%reminder Fs is 10 Hz for freq data
label = cell(size(alpha,1),1);
for t=1:size(alpha,1)
    % no pain: 1 second before inserting hand and 1 sec after end of
    % pain
    if (alpha_t(t)<floor(markers_t(1)-
1)||alpha_t(t)>ceil(markers_t(4)+1))
        label{t} = 'no pain';
        % pain: 1 second after pain marker started until removal of
hand
    elseif
(alpha_t(t)>floor(markers_t(2)+20)&&alpha_t(t)<ceil(markers_t(3)))
        label{t} = 'pain';
    else
        label{t} = 'unknown';
    end
end
clear t;
clear filen;
save(filename);
```

APPENDIX III—EXAMPLE FEATURE EVALUATION CODE

```
%% Import feature data for train and test set
clear; clc;
% % load train and test data
load('andreas_pain_2501_feat','featuresold','featuresnew');
trainset = featuresold;
andreas = featuresnew;
clear featuresold; clear featuresnew;
load('thras_pain_2501_feat','featuresold','featuresnew');
testset = featuresold;
thras = featuresnew;
clear featuresold; clear featuresnew;
X_train = trainset{:,2:end}';
X_test = testset{:,2:end}';
T_train = zeros(2,size(X_train,2));
for t = 1:size(X_train,2)
    if (strcmp(trainset.label{t},'pain'))
        T_train(1,t) = 0;
        T_train(2,t) = 1;
    else
        T_train(1,t) = 1;
        T_train(2,t) = 0;
    end
end
T_test = zeros(2,size(X_test,2));
for t = 1:size(X_test,2)
    if (strcmp(testset.label{t},'pain'))
        T_test(1,t) = 0;
        T_test(2,t) = 1;
    else
        T_test(1,t) = 1;
        T_test(2,t) = 0;
    end
end
clear t;
save('feature_evaluation_data_20');
%% Visualize data to see features that have the best separation
% Fixed standardization
[G,~] = grp2idx(andreas.label);
mean_alpha_pain = andreas.meanalpha(find(G==3));
mean_beta_pain = andreas.meanbeta(find(G==3));
mean_alpha_nopain = andreas.meanalpha(find(G==1));
mean_beta_nopain = andreas.meanbeta(find(G==1));
mean_alpha_unknown = andreas.meanalpha(find(G==2));
mean_beta_unknown = andreas.meanbeta(find(G==2));
figure
hold on
scatter(mean_alpha_pain,mean_beta_pain,'r');
scatter(mean_alpha_nopain,mean_beta_nopain,'b');
scatter(mean_alpha_unknown,mean_beta_unknown,'g');
[G,~] = grp2idx(andreas.label);
mean_alpha_pain = andreas.alpha_LE(find(G==3));
mean_beta_pain = andreas.beta_RE(find(G==3));
mean_alpha_nopain = andreas.alpha_LE(find(G==1));
mean_beta_nopain = andreas.beta_RE(find(G==1));
mean_alpha_unknown = andreas.alpha_LE(find(G==2));
mean_beta_unknown = andreas.beta_RE(find(G==2));
figure
hold on
scatter(mean_alpha_pain,mean_beta_pain,'r');
scatter(mean_alpha_nopain,mean_beta_nopain,'b');
scatter(mean_alpha_unknown,mean_beta_unknown,'g');
figure
gscatter(trainset.meanalpha,trainset.meanbeta,trainset.label,'rb');
figure
hold on
gscatter(testset.meanalpha,testset.meanbeta,testset.label,'gyoo')
gscatter(trainset.meangamma,trainset.meandelta,trainset.label,'rboo')
% have time here
figure
gplotmatrix(train{:,[2 7 12]},[ ],train.label, ...
    'br', ... %colormap
    '..', ... %style
    [ ] , ... %size of marker
    'on', ... %legend
    '', ...
    train.Properties.VariableNames([2 7 12]), ...
    train.Properties.VariableNames([2 7 12]));
figure
gplotmatrix(test{:,[2 7 12 17 22]},[ ],test.label, ...
    'br', ... %colormap
    '..', ... %style
    [ ] , ... %size of marker
    'on', ... %legend
    'hist', ...
    test.Properties.VariableNames([2 7 12 17 22]), ...
    test.Properties.VariableNames([2 7 12 17 22]));
%% Evaluate classifiers for stationary EEG classification
%   Average performance of nSamples sets for each different classifier
% Go from labels to T_train and then
nSamples = 5;
nClassifiers = 5;
class_names = {'Decision Trees','SVM RBF','SVM linear','kNN',
'Neural Network'};
crossAccu_class = zeros(nClassifiers,nSamples);
testAccu_class = zeros(nClassifiers,nSamples);
ROC_class = cell(nSamples,1);
h = waitbar(0,'Training models and validating');
for i=1:nSamples % for different number of features
    rng('shuffle');
    ind = randperm(20)+1;
    rng('shuffle');
    predictorNames = trainset.Properties.VariableNames(ind(1:randi([5
20])));
    % Run classifiers
    [crossAccu_class(1:nClassifiers-1,i), ...
        testAccu_class(1:nClassifiers-1,i), ...
        R1] = run_classifiers(trainset,testset,T_test,predictorNames);
    [crossAccu_class(nClassifiers,i), ...
        testAccu_class(nClassifiers,i), ...
        R2] =
run_neural_classifier(trainset{:,predictorNames}',T_train,
testset{:,predictor
Names}',T_test);
    ROC_class{i}{1} = R1;
    ROC_class{i}{2} = R2;
    waitbar(i/nSamples,h,sprintf('Currently at sample #%d',i))
end
close(h);
```

```
testAccu_class(1:4,:) = testAccu_class(1:4,:)/100;
[~,id] = max(testAccu_class,[ ],2);
%s = sprintf( 'class_data_%s',datestr(datetime('now')));
%save(s,'crossAccu_class','testAccu_class','id','nSamples','nClassifiers
','ROC_class','class_names');
%load('class_data_14-Feb-2015 03:32:13.mat');
% Bar graph for performances
figure
hold on
plot([1;2;3;4;5],mean(crossAccu_class,2),'*');
errorbar([1;2;3;4;5],mean(testAccu_class,2),(max(testAccu_class,[ ],2)-
min(testAccu_class,[ ],2))/2,'o');
% ROC plot
figure
hold on
for i=1:nClassifiers-1
    plot(ROC_class{id(i)}{1}{i}(:,1),ROC_class{id(i)}{1}{i}(:,2))
end
mal = ROC_class{id(end)}{2}{1};
plot(mal(1,1:size(mal,2)/2),mal(1,size(mal,2)/2+1:end))
h = ezplot( 'x',[0 1 0 1]);
set(h,'color','k')
legend(class_names)
% Optimal algorithm is kNN.
%%% Evaluate number of train features by simulation
% Average performance of nSamples sets for each different nFeat
nSamples = 100;
nFeat = 1:1:size(testset,2)-1;
crossAccu_feat = zeros(size(nFeat,2),3);
testAccu_feat = zeros(size(nFeat,2),3);
cval = zeros(nSamples,1);
tval = zeros(nSamples,1);
R = cell(nSamples,1);
ROC_feat = cell(size(nFeat,2),1);
h = waitbar(0,'Training models and cross-validating');
for i=1:size(nFeat,2) % for each number of features
    for j = 1:nSamples %run nSamples and avg
        rng('shuffle');
        tzoker = randperm(25)+1;
        predictorNames =
testset.Properties.VariableNames(tzoker(1:nFeat(i)));
        % Run optimal classifier
        kNNClassifier = fitcknn(trainset{:,predictorNames},
trainset.label, ...
                'NumNeighbors',5, ...
                'NSMethod','exhaustive', ...
                'Distance','minkowski', ...
                'PredictorNames', predictorNames, ...
                'ResponseName', 'label', ...
                'ClassNames', {'no pain' 'pain'});
        kNNcrossed = crossval(kNNClassifier,'Kfold',5);
        cval(j) = 1 - kfoldLoss(kNNcrossed, 'LossFun', 'ClassifError');
        [~,scores] = predict(kNNClassifier,testset{:,predictorNames});
        tval(j) = 1-confusion(T_test,scores');
        [X_roc, Y_roc] = perfcurve(testset.label,scores(:,2)','pain');
        R{j} = [X_roc Y_roc];
        waitbar(i/size(nFeat,2),h,sprintf('Currently at nFeat: %d,
nSample:%d',nFeat(i),j))
    end
    crossAccu_feat(i,1) = min(cval);
    crossAccu_feat(i,2) = mean(cval);
    crossAccu_feat(i,3) = max(cval);
    testAccu_feat(i,1) = min(tval);
    testAccu_feat(i,2) = mean(tval);
    [testAccu_feat(i,3),id] = max(tval);
    ROC_feat{i} = R{id};
end
close(h);
s = sprintf('feat_data_%s',datestr(datetime('now')));
save(s,'crossAccu_feat','testAccu_feat','nSamples',
'nFeat','ROC_feat');
figure
hold on
plot(nFeat,mean(crossAccu_feat,2),'*');
errorbar(nFeat,mean(testAccu_feat,2),(max(testAccu_feat,[ ],2)-
min(testAccu_feat,[ ],2))/2,'o');
%      Optimal number of features is 7
optfeatNum = 7;
%%% Evaluate features sets of size optFeat from the top 10 of the
features
% Average performance of nSamples sets for each different nFeat
all_comb = VChooseK(2:26,7);
sets = all_comb(1:2:10000,:);
nSamples = size(sets,1);
crossAccu_set = zeros(size(sets,2),1);
testAccu_set = zeros(size(sets,2),1);
ROC_set = cell(size(sets,2),1);
h = waitbar(0,'Training models and cross-validating');
for i=1:nSamples % for each number of features
    predictorNames = testset.Properties.VariableNames(sets(i,:));
    % Run optimal classifier
    kNNClassifier = fitcknn(trainset{:,predictorNames}, trainset.label,
...
            'NumNeighbors',5, ...
            'NSMethod','exhaustive', ...
            'Distance','minkowski', ...
            'PredictorNames', predictorNames, ...
            'ResponseName', 'label', ...
            'ClassNames', {'no pain' 'pain'});
    kNNcrossed = crossval(kNNClassifier,'Kfold',5);
    crossAccu_set(i) = 1 - kfoldLoss(kNNcrossed, 'LossFun',
'ClassifError');
    [~,scores] = predict(kNNClassifier,testset{:,predictorNames});
    testAccu_set(i) = 1-confusion(T_test,scores');
    [X_roc, Y_roc] = perfcurve(testset.label,scores(:,2)','pain');
    ROC_set{i} = [X_roc Y_roc];
    waitbar(i/size(sets,1),h,sprintf('Currently at set: %d',i))
end
close(h);
[~,id] = max(testAccu_set);
s = sprintf('set_data_%s',datestr(datetime('now')));
save(s,'crossAccu_set','testAccu_set','nSamples','sets','ROC_set');
optimalFeat = testset.Properties.VariableNames(sets(965,:));
figure
hold on
plot(testAccu_set)
plot(testAccu_set)
plot(testAccu_set)
%%% Classification of New Data
% Run optimal classifier
kNNClassifier = fitcknn(trainset{:,optimalFeat}, trainset.label, ...
        'NumNeighbors',5, ...
        'NSMethod','exhaustive', ...
        'Distance','minkowski', ...
        'PredictorNames', optimalFeat, ...
        'ResponseName', 'label', ...
        'ClassNames', {'no pain' 'pain'});
kNNcrossed = crossval(kNNClassifier,'Kfold',5);
crossAccu_new = 1 - kfoldLoss(kNNcrossed, 'LossFun', 'ClassifError');
[~,scores] = predict(kNNClassifier,andreas{:,optimalFeat});
T_andreas = zeros(2,size(X_test,2));
for t = 1:size(andreas,1)
    if (strcmp(andreas.label{t},'pain'))
        T_andreas(1,t) = 0;
        T_andreas(2,t) = 1;
    else
        T_andreas(1,t) = 1;
        T_andreas(2,t) = 0;
    end
end
testAccu_new = 1-confusion(T_andreas,scores');
[X_roc_new, Y_roc_new] =
perfcurve(andreas.label,scores(:,2)','pain');
ROC_set{i} = [X_roc_new Y_roc_new];
```

APPENDIX IVA—EXAMPLE FEATURE EXTRACTION CODE

```
%this file has outputs the features in a new file called
%'filename_feat'
clear;
clc;
f = load('andreas_pain_2501');
```

```
%reminder Fs is 10 Hz for freq data
filename = strcat(f.filename,'_feat');
k = 1;
varNames = {'label', ...
    'meanalpha','alphaback','alphafront','alphaleft','alpharight', ...
    'meanbeta' ,'betaback','betafront' ,'betaleft' ,'betaright', ...
    'meangamma','gammaback','gammafront',
    'gammaleft','gammaright', ...
    'meandelta','deltaback','deltafront','deltaleft','deltaright', ...
    'meantheta','thetaback','thetafront','thetaleft','thetaright' };
observations = [ ];
for t=1:size(f.alpha,1)
    if (~strcmp(f.label{t},'unknown'))
        response{k} = f.label{t};
        row = [nanmean(f.alpha(t,:)) ...
            nanmean(f.alpha(t,[1 4])) ...
            nanmean(f.alpha(t,[2 3])) ...
            nanmean(f.alpha(t,[1 2])) ...
            nanmean(f.alpha(t,[3 4])) ...
            ...
            nanmean(f.beta(t,:)) ...
            nanmean(f.beta(t,[1 4])) ...
            nanmean(f.beta(t,[2 3])) ...
            nanmean(f.beta(t,[1 2])) ...
            nanmean(f.beta(t,[3 4])) ...
            ...
            nanmean(f.gamma(t,:)) ...
            nanmean(f.gamma(t,[1 4])) ...
            nanmean(f.gamma(t,[2 3])) ...
            nanmean(f.gamma(t,[1 2])) ...
            nanmean(f.gamma(t,[3 4])) ...
            ...
            nanmean(f.delta(t,:)) ...
            nanmean(f.delta(t,[1 4])) ...
            nanmean(f.delta(t,[2 3])) ...
            nanmean(f.delta(t,[1 2])) ...
            nanmean(f.delta(t,[3 4])) ...
            ...
            nanmean(f.theta(t,:)) ...
            nanmean(f.theta(t,[1 4])) ...
            nanmean(f.theta(t,[2 3])) ...
            nanmean(f.theta(t,[1 2])) ...
            nanmean(f.theta(t,[3 4])) ];
        observations = [observations ; row];
        k = k+1;
    end
end
observations = zscore(observations);
featuresold = [cell2table(response') array2table(observations)];
featuresold.Properties.VariableNames = varNames;
observations = [ ];
for t=1:size(f.alpha,1)
    response{t} = f.label{t};
    row = [nanmean(f.alpha(t,:)) ...
        nanmean(f.alpha(t,[1 4])) ...
        nanmean(f.alpha(t,[2 3])) ...
        nanmean(f.alpha(t,[1 2])) ...
        nanmean(f.alpha(t,[3 4])) ...
        ...
        nanmean(f.beta(t,:)) ...
        nanmean(f.beta(t,[1 4])) ...
        nanmean(f.beta(t,[2 3])) ...
        nanmean(f.beta(t,[1 2])) ...
        nanmean(f.beta(t,[3 4])) ...
        ...
        nanmean(f.gamma(t,:)) ...
        nanmean(f.gamma(t,[1 4])) ...
        nanmean(f.gamma(t,[2 3])) ...
        nanmean(f.gamma(t,[1 2])) ...
        nanmean(f.gamma(t,[3 4])) ...
        ...
        nanmean(f.delta(t,:)) ...
        nanmean(f.delta(t,[1 4])) ...
        nanmean(f.delta(t,[2 3])) ...
        nanmean(f.delta(t,[1 2])) ...
        nanmean(f.delta(t,[3 4])) ...
        ...
        nanmean(f.theta(t,:)) ...
        nanmean(f.theta(t,[1 4])) ...
        nanmean(f.theta(t,[2 3])) ...
        nanmean(f.theta(t,[1 2])) ...
        nanmean(f.theta(t,[3 4])) ];
    observations = [observations ; row];
end
observations = zscore(observations);
featuresnew = [cell2table(response') array2table(observations)];
featuresnew.Properties.VariableNames = varNames;
save(filename,'featuresold','featuresnew');
```

APPENDIX IVB—EXAMPLE FEATURE EXTRACTION CODE

```
%this file has outputs the features in a new file called
%'filename_feat'
clear;
clc;
f = load('andreas_pain_2501');
%reminder Fs is 10 Hz for freq data
filename = strcat(f.filename,'_feat');
k = 1;
varNames = {'label', ...
    'alpha_LE' ,'alpha_LF' ,'alpha_RF' ,'alpha_RE', ...
    'beta_LE'  ,'beta_LF'  ,'beta_RF'  ,'beta_RE' , ...
    'gamma_LE','gamma_LF','gamma_RF','gamma_RE', ...
    'delta_LE','delta_LF','delta_RF','delta_RE', ...
    'theta_LE','theta_LF','theta_RF','theta_RE' };
observations = [ ];
for t=1:size(f.alpha,1)
    if (~strcmp(f.label{t},'unknown'))
        response{k} = f.label{t};
        row = [f.alpha(t,1) ...
            f.alpha(t,2) ...
            f.alpha(t,3) ...
            f.alpha(t,4) ...
            f.beta(t,1) ...
            f.beta(t,2) ...
            f.beta(t,3) ...
            f.beta(t,4) ...
            f.gamma(t,1) ...
            f.gamma(t,2) ...
            f.gamma(t,3) ...
            f.gamma(t,4) ...
            f.delta(t,1) ...
            f.delta(t,2) ...
            f.delta(t,3) ...
            f.delta(t,4) ...
            f.theta(t,1) ...
            f.theta(t,2) ...
            f.theta(t,3) ...
            f.theta(t,4) ...
            ];
        observations = [observations ; row];
        k = k+1;
    end
end
observations = zscore(observations);
featuresold = [cell2table(response') array2table(observations)];
featuresold.Properties.VariableNames = varNames;
observations = [ ];
for t=1:size(f.alpha,1)
    response{t} = f.label{t};
    row = [f.alpha(t,1) ...
        f.alpha(t,2) ...
        f.alpha(t,3) ...
        f.alpha(t,4) ...
        f.beta(t,1) ...
        f.beta(t,2) ...
        f.beta(t,3) ...
        f.beta(t,4) ...
        f.gamma(t,1) ...
        f.gamma(t,2) ...
        f.gamma(t,3) ...
        f.gamma(t,4) ...
```

```
            f.delta(t,1) ...
            f.delta(t,2) ...
            f.delta(t,3) ...
            f.delta(t,4) ...
            f.theta(t,1) ...
            f.theta(t,2) ...
            f.theta(t,3) ...
            f.theta(t,4) ];
    observations = [observations ; row];
end
observations = zscore(observations);
featuresnew = [cell2table(response') array2table(observations)];
featuresnew.Properties.VariableNames = varNames;
save(filename,'featuresold','featuresnew');
```

APPENDIX V—EXAMPLE NEURAL NETWORK CODE

```
function [cvalAccu, tvalAccu, ROC_class] =
run_neural_classifier(X_train,T_train,X_test,T_test)
%This function trains a neural network classifier and reports back
cross-validation and test results.
% Manipulate the data so that they are suitable for neural network
%toolbox
% We need now two matrices (arrays) input X and target T.
% Input should have rows for features and columns for observations
%(Feat × Obs).
% Target should have 2 columns, one with 1's on pain and one with 1's
%to no pain.
% Choose a Training Function
% For a list of all training functions type: help nntrain
% 'trainlm' is usually fastest.
% 'trainbr' takes longer but may be better for challenging problems.
% 'trainscg' uses less memory. Suitable in low memory situations.
trainFcn = 'trainscg'; % Scaled conjugate gradient backpropagation.
% Create a Pattern Recognition Network
hiddenLayerSize = 10;
net = patternnet(hiddenLayerSize,trainFcn);
% Choose Input and Output Pre/Post-Processing Functions
% For a list of all processing functions type: help nnprocess
net.input.processFcns = {'removeconstantrows','mapminmax'};
net.output.processFcns = {'removeconstantrows','mapminmax'};
% Setup Division of Data for Training, Validation, Testing
% For a list of all data division functions type: help nndivide
net.divideFcn = 'dividerand'; % Divide data randomly
net.divideMode = 'sample'; % Divide up every sample
net.divideParam.trainRatio = 70/100;
net.divideParam.valRatio = 15/100;
net.divideParam.testRatio = 15/100;
% Choose a Performance Function
% For a list of all performance functions type: help nnperformance
net.performFcn = 'crossentropy'; % Cross-Entropy
% Choose Plot Functions
% For a list of all plot functions type: help nnplot
net.plotFcns = {'plotperform','plottrainstate','ploterrhist', ...
'plotconfusion', 'plotroc'};
% Train the Network
[net,~] = train(net,X_train,T_train);
% Test the Network
y = net(X_train);
tind = vec2ind(T_train);
yind = vec2ind(y);
percentErrors = sum(tind ~= yind)/numel(tind);
cvalAccu = (1−percentErrors);
% View the Network
%view(net)
% Plots
% Uncomment these lines to enable various plots.
%figure, plotperform(tr)
%figure, plottrainstate(tr)
%figure, ploterrhist(e)
%figure, plotconfusion(t,y)
%figure, plotroc(t,y)
Y_test = net(X_test);
[tpr, fpr] = roc(T_test(2,:),Y_test(2,:));
ROC_class = {[fpr tpr]};
% plotconfusion(T_test,Y_test);
% plotroc(T_test,Y_test,'pain');
[c,~] = confusion(T_test,Y_test);
tvalAccu = (1−c);
end
```

APPENDIX VI—EXAMPLE INITIAL PLOTTING CODE

```
% This file plots random data from the file in different figures. It
%might help on choosing the correct features. Run it in sections!
% Use it only with new files.
%%% Data Input
clear;
clc;
% Choose filename from MuseRec/mat
filename = 'andreas_pain_2501';
f = load(sprintf('MuseRec/mat/%s',filename));
maxi = 0.2;
mini = −0.2;
%%% Alpha frequencies
figure
hold on
subplot(6,1,1)
plot(f.EEG_t,f.EEG(:,2))
line([f.markers_t(1) f.markers_t(1)],[0 1682],'color','k');
line([f.markers_t(2) f.markers_t(2)],[0 1682],'color','k');
line([f.markers_t(3) f.markers_t(3)],[0 1682],'color','k');
line([f.markers_t(4) f.markers_t(4)],[0 1682],'color','k');
subplot(6,1,2)
plot(f.alpha_t,mag2db(f.alpha(:,2)))
subplot(6,1,3)
plot(f.alpha_t,mag2db(f.beta(:,2)))
subplot(6,1,4)
plot(f.alpha_t,mag2db(f.gamma(:,2)))
subplot(6,1,5)
plot(f.alpha_t,mag2db(f.delta(:,2)))
subplot(6,1,6)
plot(f.alpha_t,mag2db(f.theta(:,2)))
line([f.markers_t(1) f.markers_t(1)],[mini maxi],'color','k');
line([f.markers_t(2) f.markers_t(2)],[mini maxi],'color','k');
line([f.markers_t(3) f.markers_t(3)],[mini maxi],'color','k');
line([f.markers_t(4) f.markers_t(4)],[mini maxi],'color','k');
%%% Plot raw data and power from sensor
fig=figure( );
s=subplot (2,1,1)
timeraw=(1:size(f.EEG,1))/220;
plot (timeraw,f.EEG(:,1))
hold on
xlabel('time [s]') % x-axis label
ylabel('Voltage [mV]') % y-axis label
title('EEG')
%is good
f.is_good(f.is_good(:,1) == 0) = NaN
timeraw2=(1:size(f.is_good,1))/10;
plot(timeraw2,f.is_good(:,1)*100+400,'LineWidth',4,'color','r')
text(0,550,' IS GOOD','color','r')
%legend
ylocation=s.YLim(2)−100;
line([f.markers_t(1) f.markers_t(1)], [s.YLim(1)
ylocation],'LineWidth',2,'color','k','LineStyle','--');
str1 = '\leftarrow Start Inducing pain';
text(f.markers_t(1),ylocation,str1)
line([f.markers_t(2) f.markers_t(2)], [s.YLim(1)
ylocation],'LineWidth',2,'color','k','LineStyle','--');
str1 = '\leftarrow Start High pain';
text(f.markers_t(2),ylocation,str1)
line([f.markers_t(3) f.markers_t(3)], [s.YLim(1)
ylocation],'LineWidth',2,'color','k','LineStyle','--');
str1 = '\leftarrow Remove Hand';
text(f.markers_t(3),ylocation,str1)
line([f.markers_t(4) f.markers_t(4)], [s.YLim(1)
```

```
ylocation],'LineWidth',2,'color','k','LineStyle','--');
str1 = '\leftarrow End pain';
text(f.markers_t(4),ylocation,str1)
s=subplot (2,1,2)
hold on
timefreq=(1:size(f.alpha,1))/10;
plot (timefreq,mag2db(f.theta(:,1)),'r','LineWidth',2,'LineStyle','-
.');
plot (timefreq,mag2db(f.delta(:,1)),'Color',[192/255 192/255
192/255],'LineWidth',1,'LineStyle','-
.','Marker','+','MarkerFaceColor','red','MarkerSize',5);
plot (timefreq,mag2db(f.alpha(:,1)),'Color',[1 0
1],'LineWidth',2,'LineStyle','-');
plot (timefreq,mag2db(f.beta(:,1)),'k','LineWidth',2,'LineStyle',':');
plot (timefreq,mag2db(f.gamma(:,1)),'b','LineWidth',2,'LineStyle','--
');
legend('theta','delta','alpha','beta','gamma','Location','best','orientation
','horizontal')
title('EEG FFT')
xlabel('time [s]') % x-axis label
ylabel('Power [dB]') % y-axis label
ylocation=s.YLim(2);
line([f.markers_t(1) f.markers_t(1)], [s.YLim(1)
ylocation],'LineWidth',2,'color','k','LineStyle','--');
str1 = '\leftarrow Start Inducing pain';
text(f.markers_t(1),ylocation,str1)
line([f.markers_t(2) f.markers_t(2)], [s.YLim(1)
ylocation],'LineWidth',2,'color','k','LineStyle','--');
str1 = '\leftarrow Start High pain';
text(f.markers_t(2),ylocation,str1)
line([f.markers_t(3) f.markers_t(3)], [s.YLim(1)
ylocation],'LineWidth',2,'color','k','LineStyle','--');
str1 = '\leftarrow Remove Hand';
text(f.markers_t(3),ylocation,str1)
line([f.markers_t(4) f.markers_t(4)], [s.YLim(1)
ylocation],'LineWidth',2,'color','k','LineStyle','--');
str1 = '\leftarrow End pain';
text(f.markers_t(4),ylocation,str1)
%Absolute band powers are based on the logarithm ...
%of the Power Spectral Density of the EEG data for ...
%each channel. Since it is a logarithm, some of the values will ...
%be negative (i.e. when the absolute power is less than 1) They are ...
%given on a log scale, units are Bels. These values are emitted at
%10Hz.
%Position 1: Left Ear(TP9), Range: 0.0 - 1682.0 in microvolts
%theta (1-4Hz), delta (5-8Hz), alpha (9-13Hz), beta (13-30Hz), gamma
%(30-50Hz) a
```

APPENDIX VII—EXAMPLE MUSE CODE

```
classdef museliveplot < handle
    % museliveplot An app written with a MATLAB class to plot
    % incoming EEG data.
    properties
        Figure              % Graphics handles
        Axis
        Line
        TickerText
        TickerEdit
        Timer               % Timer object to get updated
        TimerUpdateRate = 1/220   % prices In seconds
        NumValues = 1000          % Number of values shown
    end                            in the plot
    methods
        function app = museliveplot
            % This is the "constructor" for the class
            % It runs when an object of this class is created
            app.Figure = figure('MenuBar','none',...
% Main figure
                'NumberTitle','off','Name','Simple Stock Ticker',...
                'CloseRequestFcn',@app.closeApp) ;
            app.Axis = axes('Parent',app.Figure,...
% Axis for prices
                'Position',[.13 .15 .78 .75]);
            app.TickerText = uicontrol(app.Figure,...
% 'Symbol' label
                'Style','text','Position',[20 20 50 20],...
                'String','Symbol:');
            app.TickerEdit = uicontrol(app.Figure,...
% Symbol edit box
                'Style','edit','Position',[75 20 50 20 ],...
                'String',app.TickerSymbol,...
                'Callback', @app.symbolUpdateCallback);
            prices = NaN*ones(1,app.NumValues) ;
% Initialize prices
            app.Line = plot(app.Axis,prices,'Marker',...
                '.','LineStyle','-');
            ylabel(app.Axis,'Stock value ($)') ;
            set(app.Axis,'XTickLabel','') ;
            title(app.Axis,['Stock Price: ' app.TickerSymbol])
            app.Timer = timer;
% Create timer
            app.Timer.ExecutionMode = 'fixedRate' ;
            app.Timer.Period = app.TimerUpdateRate ;
            app.Timer.TimerFcn = @app.valueUpdateCallback ;
            start(app.Timer) ;
        end
        function closeApp(app,hObject,eventdata)
            % This function runs when the app is closed
            try
                stop(app.Timer)
                delete(app.Timer)
            end
            delete(app.Figure)
        end
        function symbolUpdateCallback(app,hObject,eventdata)
            % This function runs when ticker changes in edit box
            set(app.Line,'YData',NaN*ones(1,app.NumValues));
            app.TickerSymbol = get(app.TickerEdit,'String');
            [price,name] = getQuote(app) ;
            if price == 0
                warndlg(['Ticker symbol ' app.TickerSymbol ' not
found'])
            end
            title(app.Axis,['Stock Price: ' name])
            valueUpdateCallback(app)
        end
        function valueUpdateCallback(app,hObject,eventdata)
            % This function runs when the timer updates
            StockSymbol = app.TickerSymbol;
            try
                price = getQuote(app) ;
            catch
                errordlg(['Could not retrieve price for ' StockSymbol])
            end
            yvalues = get(app.Line,'YData');
% Update the plot
            yvalues = [yvalues(2:end) price];
            set(app.Line,'YData',yvalues)
        end
        function [value,name] = getQuote(app)
            % getQuote(app) Get stock quote using simple
Yahoo finance %API.
            % See http://www.gummy-stuff.org/Yahoo-data.htm
            %     for details
%           url =
%sprintf('http://finance.yahoo.com/d/quotes.csv?s=%s&f=n1l',...
%               app.TickerSymbol);
%           s = urlread(url);
            [name,remain] = strtok(s,'"');
            value = str2num(strtok(remain,'",'));
        end
    end
end
% End of class definition
```

What is claimed is:

1. A system for classifying perceptual states comprising:
an EEG sensor and signal conditioning platform;
a classifier, the classifier constructed using EEG data of only a single user; and
a mobile neurofeedback apparatus coupled to the signal conditioning platform comprising:

an input interface constructed to allow the single user to enter a first single user time-stamped marker on first EEG data taken from only the single user, the single user marker configured to be used in the classifier for machine learning of arbitrary, user-defined perceptual brain states, the classifier constructed to receive and operate on second EEG data from the single user, the single user marker entered for one arbitrary, user-defined perceptual brain state perceived only by the single user during a calibration phase;

a processor configured to predict the one arbitrary, user-defined perceptual brain state for the same single user by using the classifier to analyze incoming second EEG signals of the same single user during an operational phase and to generate a classification result; and a display configured for viewing of EEG data and the classification result;

wherein the classifier is further constructed to be a multi-class classifier to receive a second single user marker entered for at least one additional arbitrary, user-defined perceptual brain state opposite the one arbitrary, user-defined perceptual brain state;

and wherein the classifier also classifies non-binary intermediate brain states between the one arbitrary, user-defined perceptual brain state and the one additional arbitrary, user-defined perceptual brain state.

2. The system of claim 1, wherein the classifier is a maximum posterior probability classifier.

3. The system of claim 1, wherein the classification result is refined through a feedback loop in which the single user answers whether the classifier has correctly predicted one or more perceptual brain states.

4. The system of claim 1, wherein the classifier is a k-nearest neighbor classifier.

5. The system of claim 1, wherein the classifier uses a Fast-Fourier transform (FFT) to separate alpha frequency responses from beta frequency responses.

6. The system of claim 5, wherein the FFT is a short FFT taken every 22 samples with a window of 256 producing feature vectors at a rate of 10 observations per second.

7. The system of claim 1, further comprising a link between the signal conditioning platform and the neurofeedback apparatus, wherein the link is wireless.

8. The system of claim 1, wherein the classifier includes a machine learning algorithm, the machine learning algorithm chosen from one of k-nearest neighbor, support vector machines, neural networks, or decision trees.

9. An apparatus for classifying perceptual states, comprising:
an EEG sensor and signal conditioning platform;
a classifier, the classifier constructed using EEG data of only a single user; and
a mobile neurofeedback apparatus comprising:
an input interface for allowing the single user to enter time-stamped markers on first EEG data from the single user, the time-stamped markers used in a classifier for machine learning of arbitrary, user-defined perceptual brain states;
a processor to generate the classifier for the prediction of an arbitrary, user-defined perceptual brain state from a second EEG signal from the same single user, and to generate a classification result based on said first EEG data and said time-stamped markers from the same single user;
a display configured for viewing of the second EEG signal and the classification result; and
a link between the EEG sensor and neurofeedback apparatus;
wherein the classifier is further constructed to receive a second single user marker entered for at least one additional arbitrary, user-defined perceptual brain state opposite the one perceptual brain state;
and wherein the classifier also classifies non-binary intermediate brain states between the one arbitrary, user-defined perceptual brain state and the one additional arbitrary, user-defined perceptual brain state.

* * * * *